(12) United States Patent
Oouchi

(10) Patent No.: US 9,139,806 B2
(45) Date of Patent: Sep. 22, 2015

(54) MICROBIAL COUNTING CELL, MICROBE COUNTING DEVICE USING SAME, AND MICROBE COUNTING METHOD USING SAME

(75) Inventor: Kazufumi Oouchi, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

(21) Appl. No.: 13/575,037

(22) PCT Filed: Aug. 29, 2011

(86) PCT No.: PCT/JP2011/004776
§ 371 (c)(1),
(2), (4) Date: Jul. 25, 2012

(87) PCT Pub. No.: WO2012/029273
PCT Pub. Date: Mar. 8, 2012

(65) Prior Publication Data
US 2012/0288890 A1    Nov. 15, 2012

(30) Foreign Application Priority Data

Aug. 30, 2010  (JP) .................. 2010-191809
Oct. 18, 2010  (JP) .................. 2010-233222
Oct. 18, 2010  (JP) .................. 2010-233223

(51) Int. Cl.
*C12M 1/34*    (2006.01)
*C12M 1/26*    (2006.01)
(Continued)

(52) U.S. Cl.
CPC ............. *C12M 41/36* (2013.01); *B01L 3/5029* (2013.01); *G01N 15/0656* (2013.01); *B01L 2300/0609* (2013.01); *B01L 2300/0851* (2013.01); *G01N 2001/028* (2013.01)

(58) Field of Classification Search
CPC ................ C12M 41/36; B01L 3/5029; B01L 2300/0609; B01L 2300/0851; G01N 15/0656; G01N 2001/028
USPC ....................... 435/39, 287.1, 309.1
See application file for complete search history.

(56) References Cited

U.S. PATENT DOCUMENTS 3,518,164 A *  6/1970  Andelin et al. ............. 435/30
7,932,082 B2    4/2011  Abraham-Fuchs et al.
(Continued)

FOREIGN PATENT DOCUMENTS

CN    1967195 A    5/2007
JP    2009-210488 A    9/2009
(Continued)

OTHER PUBLICATIONS

International Search Report for PCT/JP2011/004776, Nov. 8, 2011.
(Continued)

*Primary Examiner* — William H Beisner
*Assistant Examiner* — Danielle Henkel
(74) *Attorney, Agent, or Firm* — RatnerPrestia

(57) ABSTRACT

A microorganism counting cell of the present invention includes bottomed cylindrical vessel that includes upper surface opening and cylindrical retaining body disposed vertically on a bottom surface in vessel, a collecting element provided on a lower end portion of a rod-shaped cotton swab being inserted in retaining body from upper surface opening. In the microorganism counting cell, elution protrusion is provided on an interior side surface of retaining body, and elution groove that pierces retaining body from an inside to an outside is provided on a side surface of retaining body.

20 Claims, 36 Drawing Sheets

(51) Int. Cl.
  *G01N 27/26*  (2006.01)
  *B01L 3/00*  (2006.01)
  *G01N 15/06*  (2006.01)
  *G01N 1/02*  (2006.01)

(56) References Cited

U.S. PATENT DOCUMENTS

| | | | | |
|---|---|---|---|---|
| 2005/0019875 A1* | 1/2005 | Chen | ............................ | 435/91.2 |
| 2008/0193926 A1* | 8/2008 | Abraham-Fuchs et al. | ...... | 435/6 |
| 2009/0030342 A1* | 1/2009 | Flanigan et al. | ............... | 600/572 |
| 2010/0111773 A1* | 5/2010 | Pantelidis | ..................... | 422/102 |

FOREIGN PATENT DOCUMENTS

JP   2010-038640 A   2/2010
WO   WO 2009/018014 A1   2/2009

OTHER PUBLICATIONS

CN Office Action for 201180022418.7, Jul. 29, 2013.

* cited by examiner

MICROBIAL COUNTING CELL, MICROBE COUNTING DEVICE USING SAME, AND MICROBE COUNTING METHOD USING SAME

TECHNICAL FIELD

The present invention relates to a microorganism counting cell that measures, for example, the number of microorganisms existing in an oral cavity or the number of microorganisms adhering to food.

BACKGROUND ART

Conventionally, this kind of microorganism counting cell has the following structure.

Specifically, the microorganism counting cell includes a bottomed cylindrical vessel that is provided with an upper surface opening, and a rotor that is provided on the vessel. In a configuration of the microorganism counting cell, a collecting element that is provided on a lower end portion of a rod-shaped microorganism collecting tool is inserted from the upper surface opening of the vessel, and the rotor provided on a bottom surface in the vessel is rotated to strike the collecting element, thereby eluting the microorganisms of the collecting element in a liquid of the vessel (for example, see PTL 1).

Then, the number of microorganisms eluted in the liquid is measured.

Here, the liquid is previously put in the vessel, or the liquid is put in the vessel after the collecting element provided on the lower end portion of the microorganism collecting tool is inserted in the vessel.

In the conventional microorganism counting cell, usefully the microorganisms of the collecting element are eluted in the liquid such that the rotor is rotated to strike the collecting element. However, unfortunately it takes a long time to strike the collecting element to take out the microorganisms from the collecting element, and therefore an elution time is lengthened.

That is, in the conventional microorganism counting cell, the microorganisms are eluted in the liquid of the vessel such that the rotor provided on the bottom surface in the vessel is rotated to strike the rod-shaped microorganism collecting tool, a lower portion of the collecting element is struck by the rotor provided on the bottom surface in the vessel, and sometimes many microorganisms are collected from an intermediate portion to an upper portion of the collecting element depending on a collecting state of a user.

Therefore, it takes a long time to elute the microorganisms from the portion that is not struck by the rotor. The present invention is devised to shorten the microorganism elution time.

CITATION LIST

Patent Literature

PTL 1: Unexamined Japanese Patent Publication No. 2009-210488

SUMMARY OF THE INVENTION

A microorganism counting cell of the present invention includes: a bottomed cylindrical vessel that includes an upper surface opening; and a cylindrical retaining body disposed vertically on a bottom surface in the vessel for receiving a collecting element provided on a lower end portion of a rod-shaped microorganism collecting tool being inserted in the retaining body from the upper surface opening, wherein a plurality of first elution protrusions of a longwall shape formed in an axial direction of the retaining body at predetermined intervals around an interior side surface of the retaining body, and elution grooves, each formed to cut through a side surface of the retaining body from the inside to the outside between adjoining two of the plurality of first elution protrusions.

DESCRIPTION OF EMBODIMENTS

First Exemplary Embodiment

Hereinafter, by way of example, an exemplary embodiment of the present invention applied to a microorganism counting cell that measures the number of microorganisms (bacteria) existing in an oral cavity will be described below with reference to the drawings.

Figure 1:
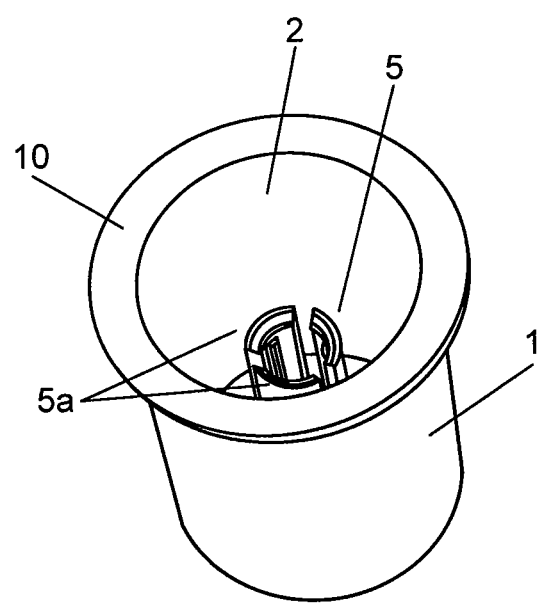
FIG. 1 is a perspective view illustrating a microorganism counting cell according to an exemplary embodiment of the present invention.

Referring to FIG. 1, bottomed cylindrical vessel 1 is made of a synthetic resin such as polycarbonate, and circular upper surface opening 2 is formed in an upper surface of vessel 1.

Figure 2A:
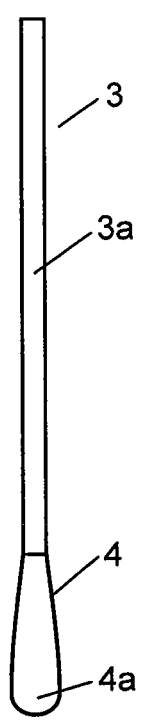
FIG. 2A is a side view illustrating a microorganism collecting tool that is used in use of a microorganism counting cell according to an exemplary embodiment of the present invention.
Figure 2B:
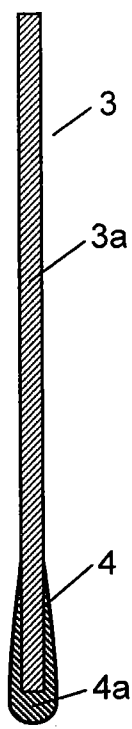
FIG. 2B is a sectional view illustrating the microorganism collecting tool that is used in use of the microorganism counting cell according to the exemplary embodiment of the present invention.
Figure 2C:
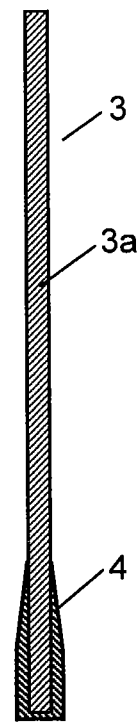
FIG. 2C is a sectional view illustrating the microorganism collecting tool that is used in use of the microorganism counting cell according to the exemplary embodiment of the present invention.

Rod-shaped microorganism collecting tool illustrated in FIGS. 2A to 2C such as cotton swab 3 is inserted in upper surface opening 2. Cylindrical retaining body 5 disposed vertically on a bottom surface of vessel 1, and collecting element 4 provided on a lower end portion of inserted cotton swab 3 is inserted in cylindrical retaining body 5. In order to facilitate the insertion of collecting element 4 of cotton swab 3, the upper surface of cylindrical retaining body 5 constitutes a circular opening in which an obstacle such as a beam does not exist.

In cotton swab 3, as illustrated in FIGS. 2A and 2B, cotton collecting element 4 is provided on a lower end portion of rod 3a, and swab portion 4a having a diameter larger than that of rod 3a is formed at a lower end of collecting element 4.

Figure 3A:
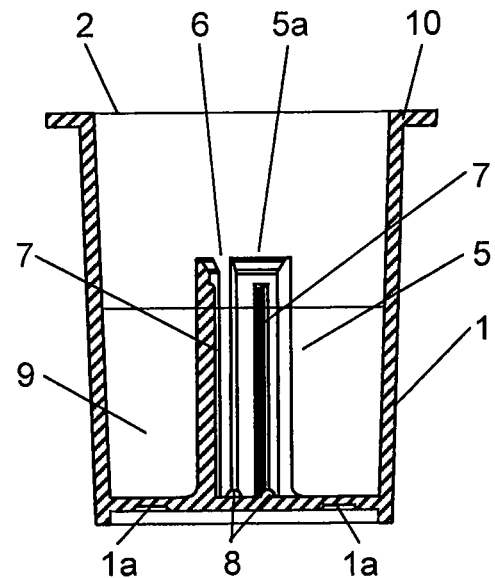
FIG. 3A is a longitudinal sectional view illustrating a microorganism counting cell according to an exemplary embodiment of the present invention.
Figure 3B:
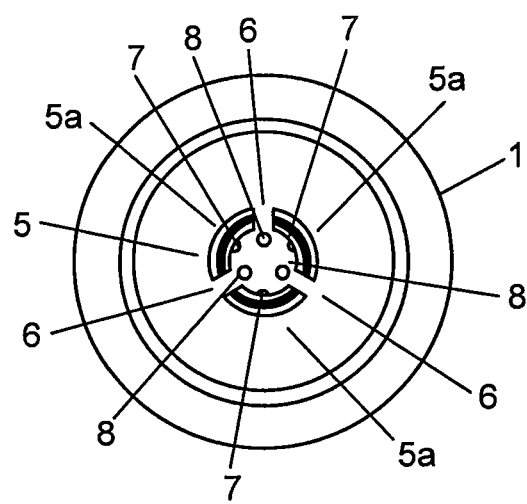
FIG. 3B is a top view illustrating the microorganism counting cell according to the exemplary embodiment of the present invention.

FIG. 3A is a longitudinal sectional view of vessel 1, and FIG. 3B is a top view of vessel 1. As illustrated in FIGS. 3A and 3B, retaining body 5 includes a plurality of (three) side surface bodies 5a disposed vertically at predetermined equal intervals on a bottom surface of vessel 1 and a plurality of (three) longwall-shaped elution protrusions 7 that are provided on an axial direction of retaining body 5 in interior side surfaces of side surface bodies 5a.

Among the plurality of (three) side surface bodies 5a constituting retaining body 5, a plurality of (three) elution grooves 6 each of which pierces retaining body 5 from the inside to the outside are formed into a thin, long groove from the bottom surface to upper surface of retaining body 5.

That is, the side surface of retaining body 5 extends in the axial direction of retaining body 5, and the side surface is divided into three side surface bodies 5a while sandwiched among three elution grooves 6 disposed at predetermined equal intervals. In the inner side surfaces of side surface bodies 5a, elution protrusions 7 are provided on central portions in a circumferential direction of side surface body 5a, respectively.

As illustrated in FIG. 3B, in an interior bottom surface of retaining body 5, a plurality of (three) elution protrusions 8 are provided circularly at equal intervals around an axis center of retaining body 5. Elution protrusion 8 is formed into a hemispherical shape while an upper-surface side of elution protrusion 8 has a spherical surface.

Figure 4:
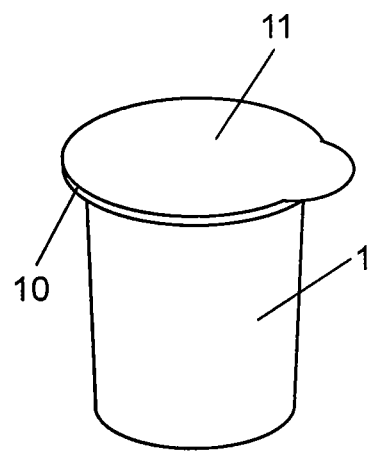
FIG. 4 is a perspective view illustrating a microorganism counting cell according to an exemplary embodiment of the present invention in an unused state.

A measurement liquid (for example, pure water 9) is stored in vessel 1 as illustrated in FIG. 3A, and aluminum cover body 11 is detachably welded to step portion 10 formed in upper surface opening 2 of vessel 1 in order to seal vessel 1 as illustrated in FIG. 4. Vessel 1 is retained and managed while sealed.

Figure 5:
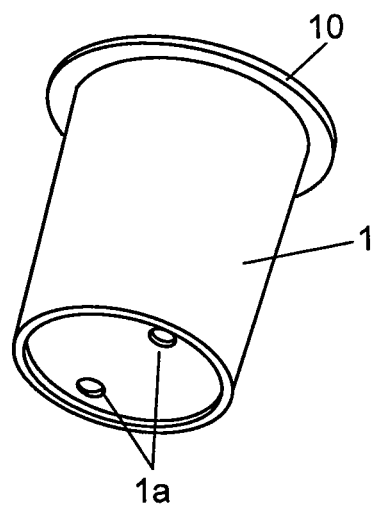
FIG. 5 is a perspective view illustrating a microorganism counting cell according to an exemplary embodiment of the present invention when viewed from below.

As illustrated in FIG. 5, on the outside of the bottom surface of vessel 1, two fixing holes 1a that does not pierce the bottom portion of vessel 1 are symmetrically made with respect to the center axis of cylindrical vessel 1 as a fixing portion for fixing vessel 1 to an external device.

Figure 6:
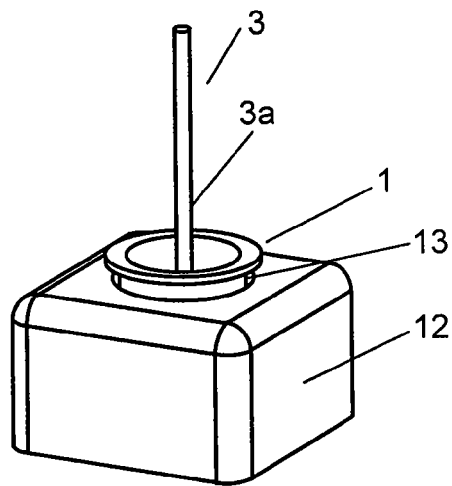
FIG. 6 is a perspective view illustrating a microorganism counting cell according to an exemplary embodiment of the present invention in use.

FIGS. 6 to 11 illustrate a state in which a measurer elutes microorganisms (bacteria) included in cotton swab 3 in a microorganism counting cell of the first exemplary embodiment. First, the measurer detaches cover body 11 (FIG. 4) that covers upper surface opening 2 of vessel 1 from vessel 1, and mounts vessel 1 on mounting unit 13 provided on the upper surface of vessel support 12 as illustrated in FIG. 6.

Figure 7:
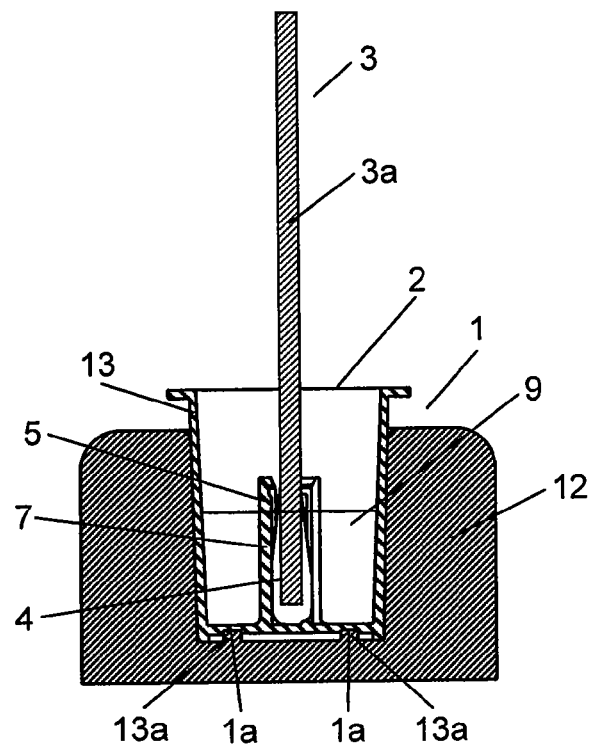
FIG. 7 is a sectional view illustrating a microorganism counting cell according to an exemplary embodiment of the present invention in use.

As illustrated in FIG. 7, two projections 13a provided on the inner bottom portion of mounting unit 13 are fitted in two fixing holes 1a made on the outside of the bottom surface of vessel 1, thereby mounting vessel 1 on mounting unit 13.

Then, the measurer traces a tongue of a subject to collect the bacteria in the oral cavity with collecting element 4 provided on the lower end portion of rod 3a of cotton swab 3 in FIG. 2.

Then, the measurer inserts collecting element 4 in cylindrical retaining body 5 from upper surface opening 2 of vessel 1 as illustrated in FIG. 7.

Figure 8:
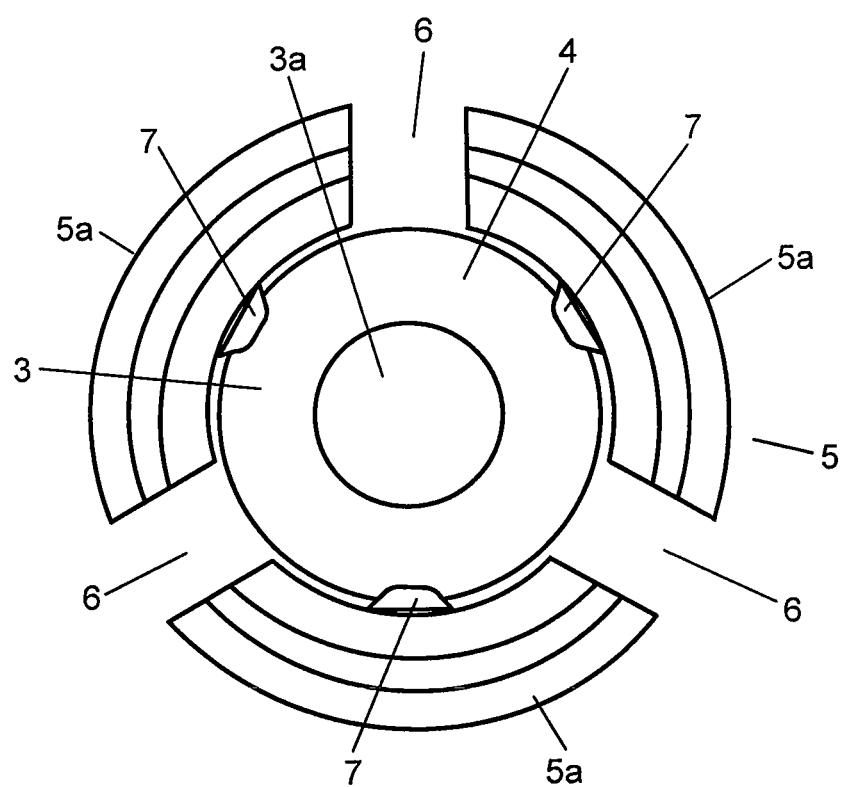
FIG. 8 is an enlarged top view illustrating a main part of a microorganism counting cell according to an exemplary embodiment of the present invention in use.

FIG. 8 is a view illustrating the state in which collecting element 4 of cotton swab 3 is inserted in retaining body 5 when viewed from above. Cylindrical retaining body 5 is configured such that the side surface of collecting element 4 of cotton swab 3 is retained while abutting on three elution protrusions 7 provided on the interior side surfaces of side surface bodies 5a constituting retaining body 5.

Therefore, collecting element 4 is inserted while abutting on three longwall-shaped elution protrusions 7 provided on the inner wall surfaces of side surface bodies 5a, and the measurer is guided by three longwall-shaped elution protrusions 7 while feeling insertion resistances of elution protrusions 7 through rod 3a of cotton swab 3, whereby the measurer inserts collecting element 4 in retaining body 5.

As a result, the side surface of collecting element 4 of cotton swab 3 is firmly retained at equal intervals by three longwall-shaped elution protrusions 7 that are provided on the axial direction of retaining body 5.

Figure 9:
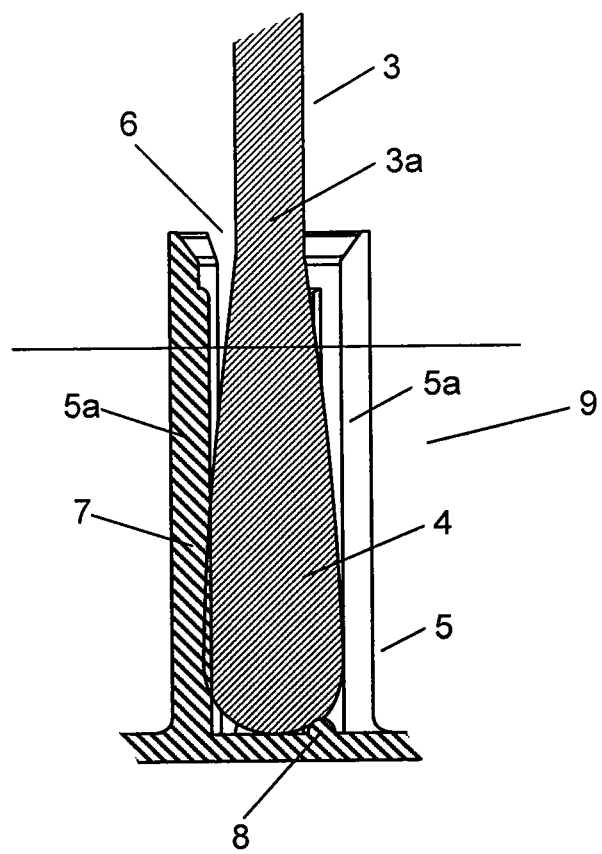
FIG. 9 is an enlarged sectional view illustrating a main part of a microorganism counting cell according to an exemplary embodiment of the present invention in use.

At this point, as illustrated in FIG. 9, collecting element 4 is retained by retaining body 5 while dipped in pure water 9 of vessel 1.

As can be seen from FIG. 9, when collecting element 4 is inserted in retaining body 5, a side portion from the lower portion to intermediate portion of collecting element 4 abuts on elution protrusions 7. At this point, collecting element 4 is swollen by containing pure water 9, and the whole side portion from the lower portion to upper portion of collecting element 4 abuts on longwall-shaped elution protrusions 7 that are provided on the inner wall surfaces of side surface bodies 5a while a frictional force is increased.

The side portion of collecting element 4 abuts firmly on longwall-shaped elution protrusions 7. For example, when rod 3a is held to lift cotton swab 3, the side portion of collecting element 4 abuts so firmly on longwall-shaped elution protrusions 7 that vessel 1 retaining pure water 9 is lifted while attached to cotton swab 3.

Figure 10:
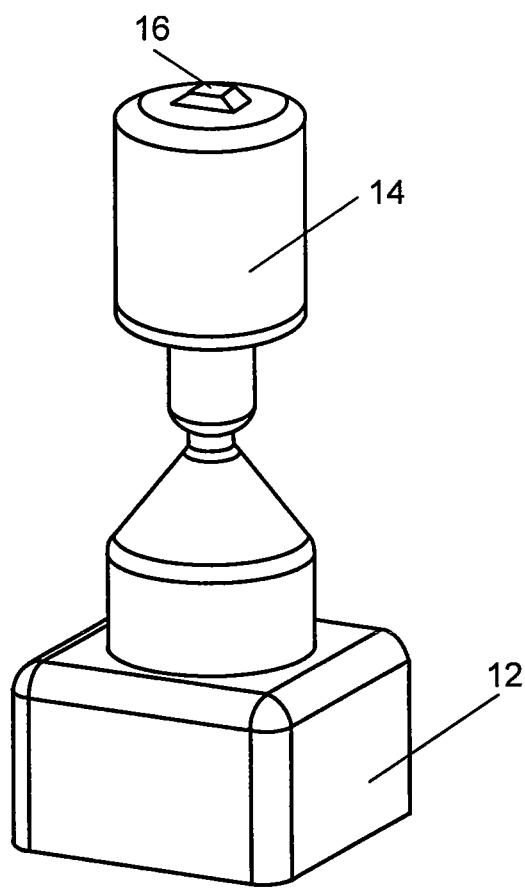
FIG. 10 is a perspective view illustrating a microorganism counting cell according to an exemplary embodiment of the present invention in use.
Figure 11:
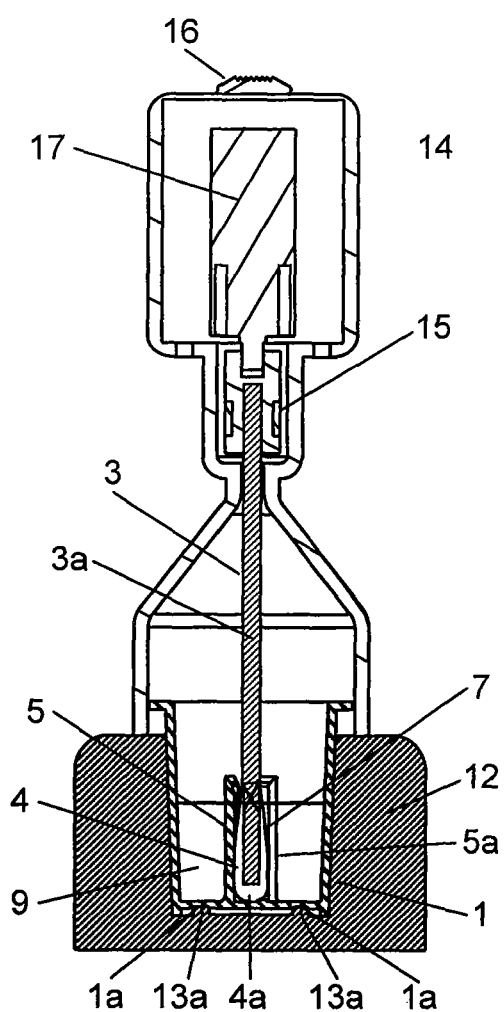
FIG. 11 is a sectional view illustrating a microorganism counting cell according to an exemplary embodiment of the present invention in use.

Then, as illustrated in FIG. 10, when the lower portion of rotation tool 14 is placed from above cotton swab 3 so as to abut on the upper surface of vessel support 12, the upper portion of cotton swab 3 is inserted while forced against cotton swab mounting unit 15 in rotation tool 14 as illustrated in FIG. 11.

The upper portion of cotton swab 3 is retained by cotton swab mounting unit 15, and cotton swab 3 is mounted on rotation tool 14 connected to cotton swab mounting unit 15.

When cotton swab 3 is mounted on rotation tool 14, because cotton swab 3 is pushed down by cotton swab mounting unit 15, swab portion 4a formed at the lower end of collecting element 4 of cotton swab 3 is pushed down toward the interior bottom surface of retaining body 5, and swab portion 4a abuts firmly on three elution protrusions 8 (FIG. 3B) provided on the interior bottom surface while being compressed between the interior bottom surface of vessel 1 and the lower end portion of rod 3a.

When switch 16 of rotation tool 14 is pressed in this state, motor 17 in rotation tool 14 rotates, cotton swab 3 rotates through cotton swab mounting unit 15, and collecting element 4 provided on the lower end portion of cotton swab 3 rotates in retaining body 5.

At this point, in retaining body 5, the whole side portion from the lower portion to upper portion of collecting element 4 is retained by abutting on longwall-shaped elution protrusions 7 formed in three side surface bodies 5a from three directions at predetermined equal intervals.

Therefore, collecting element 4 rotates stably while being retained equal intervals by abutting on elution protrusions 7 from the three directions, and the whole side portion of collecting element 4 are sequentially scrubbed to longwall-shaped elution protrusions 7 provided on three side surface bodies 5a. The scrub elutes the bacteria from collecting element 4 such that the bacteria collected by collecting element 4 are scraped.

At this point, the whole side portion of collecting element 4 abuts on elution protrusion 7, and the portion from the intermediate portion to lower portion of collecting element 4 is enlarged compared with the upper portion of collecting element 4 as illustrated in FIG. 2.

Due to this, at the beginning of the rotation, the portion from the intermediate portion to lower portion of collecting element 4 is strongly scrubbed to elution protrusion 7 compared with the upper portion of collecting element 4. Therefore, the cotton constituting collecting element 4 moves toward the upper portion having a low scrubbing pressure along the side portion of rod 3a.

When cotton swab 3 continuously rotates to scrub collecting element 4 to elution protrusion 7, collecting element 4 is deformed such that the scrubbing pressure between collecting element 4 and elution protrusion 7 is uniformed in the side portion of collecting element 4, namely, a thickness of the cotton is kept constant. The cotton in which the thickness is kept constant by the deformation is scrubbed to longwall-shaped elution protrusion 7, and the bacteria elution is promoted by applying the substantially same force from the lower portion to upper portion of collecting element 4, thereby efficiently eluting the bacteria.

When the scrub is further continued in this state, the cotton of collecting element 4 is wrung around rod 3a with a uniform thickness, and the bacteria collected in the cotton are finally eluted into pure water 9 so as to be squeezed from collecting element 4.

On the other hand, as illustrated in FIG. 8, swab portion 4a formed at the lower end of collecting element 4 is compressed between the interior bottom surface of retaining body 5 and the lower end portion of rod 3a, and abuts on three hemispherical elution protrusions 8 provided on the interior bottom surface.

Therefore, when collecting element 4 rotates, swab portion 4a is sequentially scrubbed to three elution protrusions 8, and the scrub can elite the bacteria collected by swab portion 4a from collecting element 4 in a short period of time.

At this point, the cotton constituting swab portion 4a moves in the direction of the side portion of rod 3a having the low scrubbing pressure.

When swab portion 4a is continuously scrubbed to elution protrusions 8 in this state, the cotton of swab portion 4a and the cotton in the side portion of collecting element 4 are scrubbed to longwall-shaped elution protrusions 7 in the side portion of rod 3a.

Finally, as illustrated in FIG. 2C, swab portion 4a is scrubbed to elution protrusions 8 and eliminated.

On the other hand, the cotton of collecting element 4 is also wrung until wound around rod 3a with the uniform thickness.

As a result, all the bacteria collected by collecting element 4 are eluted to the outside of collecting element 4.

As illustrated in FIGS. 8 and 9, because thin, long elution groove 6 is provided from the bottom surface to upper surface in the side surface of retaining body 5, the bacteria eluted from collecting element 4 go out from retaining body 5 through nearest elution groove 6 facing collecting element 4, and the bacteria can be immediately eluted into pure water 9 of vessel 1.

At this point, it is necessary that almost all the bacteria included in collecting element 4 be taken out in order to measure, for example, the number of microorganisms existing in the oral cavity or the number of microorganisms adhering to food.

In the first exemplary embodiment, as described above, when collecting element 4 rotates while being inserted in retaining body 5, the whole side portion from the lower portion to upper portion of collecting element 4 abuts on longwall-shaped elution protrusions 7 formed in three side surface bodies 5a in retaining body 5.

Accordingly, when collecting element 4 continuously rotates, the whole side portion of collecting element 4 is sequentially scrubbed to longwall-shaped elution protrusions 7 provided on three side surface bodies 5a. Almost all the bacteria of collecting element 4 can be eluted into pure water 9 of vessel 1 in a short period of time by the scrub.

As a result, the bacteria can efficiently be taken out from collecting element 4 to shorten the bacteria elution time.

Then, when the rotation of motor 17 in FIG. 11 is stopped to lift rotation tool 14, cotton swab 3 mounted on rotation tool 14 can easily be extracted from retaining body 5 for the following reason.

Before the elution, collecting element 4 of cotton swab 3 abuts firmly on retaining body 5. In order to elute the bacteria, when cotton swab 3 is rotated to scrub collecting element 4 to elution protrusion 7 and elution protrusion 8, collecting element 4 is wrung and wound around rod 3a as illustrated in FIG. 2C.

In this state, because collecting element 4 of cotton swab 3 is not already retained by retaining body 5, cotton swab 3 can easily be extracted from retaining body 5.

Then, vessel 1 including pure water 9 in which the bacteria are eluted is taken out from vessel support 12, and vessel 1 is set in a measurement instrument (not illustrated) to measure the number of bacteria.

Figure 12A:
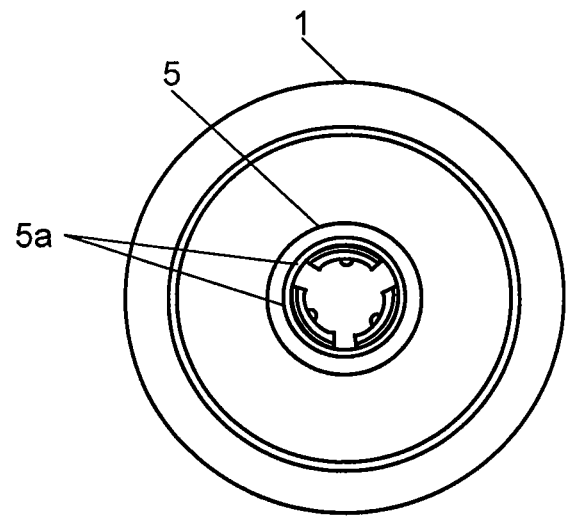
FIG. 12A is a top view illustrating a microorganism counting cell according to an exemplary embodiment of the present invention.
Figure 12B:
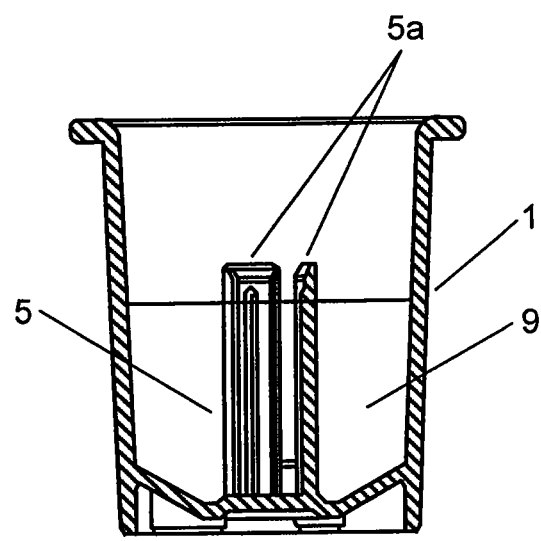
FIG. 12B is a longitudinal sectional view illustrating the microorganism counting cell according to the exemplary embodiment of the present invention.

In the first exemplary embodiment, elution protrusions 8 are provided on the interior bottom surface of retaining body 5 in addition to three longwall-shaped elution protrusions 7 provided on the inner wall surfaces of side surface bodies 5a. Alternatively, because the bacteria can sufficiently be eluted into pure water 9 only by elution protrusions 7, elution protrusions 8 may be eliminated from the interior bottom surface of retaining body 5 as illustrated in FIGS. 12A and 12B.

Other features of the first exemplary embodiment will be described below.

In the first exemplary embodiment, as described above, the side surface of retaining body 5 is divided into three side surface bodies 5a, and side surface bodies 5a are configured to be vertically provided on the bottom surface of vessel 1.

When rod-shaped cotton swab 3 is rotated at a high speed of, for example, 100 rps, sometimes cotton swab 3 is rotated while deviated from the rotation center by a centrifugal force. Even such cases, side surface body 5a is fixed to the bottom surface of vessel 1 only at the lower end, so that the upper portion of vessel 1 can be deflected toward the outside of the rotation center.

Therefore, side surface body 5a properly allows an excessive pressure generated by the rotation of cotton swab 3 to escape, and collecting element 4 can be scrubbed to elution protrusions 7 with a proper pressure.

As described above, because the excessive pressure is not partially applied to collecting element 4 of cotton swab 3, the cotton of collecting element 4 is not broken by elution protrusions 7, and the cotton does not go out into pure water 9. Therefore, the broken cotton of collecting element 4 does not adversely affect the measurement of the number of bacteria, which is performed after the bacteria elution.

As a result, the bacteria can be eluted from collecting element 4 in a short period of time, for example, 10 seconds to shorten the bacteria elution time.

As illustrated in FIG. 5, on the outside of the bottom surface of vessel 1, two fixing holes 1a are symmetrically made with respect to the center axis of cylindrical vessel 1 as a fixing portion for fixing vessel 1 to the external device. Two projections 13a provided on the inner bottom portion of mounting unit 13 of vessel support 12 in FIG. 7 are fitted in two fixing holes 1a. Therefore, even when cotton swab 3 is rotated at a high speed of, for example, 100 rps, the rotation of vessel 1 can be prevented without being affected from the rotation of cotton swab 3.

As a result, rotating cotton swab 3 can firmly be scrubbed to elution protrusions 7 of three still side surface bodies 5a to shorten the bacteria elution time.

Further, in the first exemplary embodiment, the plurality of (three) elution protrusions 8 are provided at equal intervals on the circle around the axis center of retaining body 5 in the interior bottom surface of retaining body 5 of vessel 1.

Swab portion 4a in the lower end portion of rod 3a of cotton swab 3 is forced against three elution protrusions 8. Therefore, swab portion 4a is retained by three elution protrusions 8 in the bottom surface.

When cotton swab 3 is rotated, the lower end portion of rod 3a that forces swab portion 4a against three elution protrusions 8 is rotated while guided to the axis center of retaining body 5 by three elution protrusions 8.

Particularly, because three elution protrusions 8 are formed into the hemispherical shape, the lower end portion of rod 3a is smoothly guided to the axis center of retaining body 5 by utilizing a curved surface of the hemisphere.

The rotation of cotton swab 3 can be stabilized by the above configuration.

As a result, because of the stabilization of the rotation of cotton swab 3, the bacteria can be eluted, and the bacteria elution time can be shortened.

In the first exemplary embodiment, the measurement of the number of bacteria existing in the oral cavity is described by way of example. The present invention can also be applied to the microorganism counting cell that measures the number of microorganisms adhering to the food.

In the first exemplary embodiment, rod 3a of cotton swab 3 is rotated. Alternatively, as illustrated in FIG. 13, rod 3a of cotton swab 3 may be taken between fingers to rotate vessel 1.

That is, even if vessel 1 is rotated instead of rotating cotton swab 3, because elution protrusions 7 of retaining body 5 can be scrubbed to collecting element 4 of cotton swab 3, the bacteria collected by collecting element 4 of cotton swab 3 can be eluted into pure water 9 in a short period of time similarly to the first exemplary embodiment.

Figure 13:
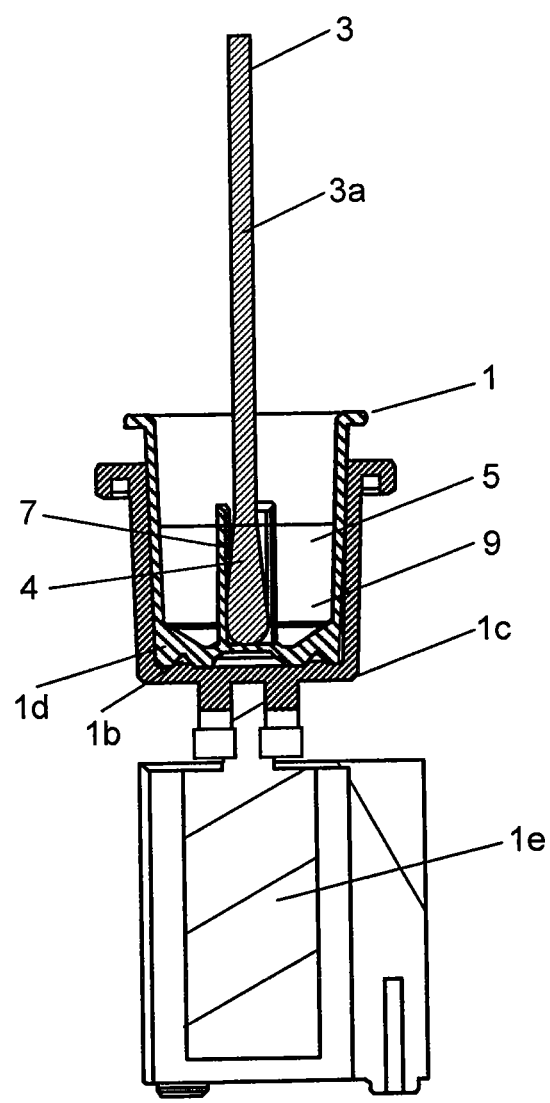
FIG. 13 is a sectional view illustrating a microorganism counting cell according to an exemplary embodiment of the present invention in use.
Figure 14:
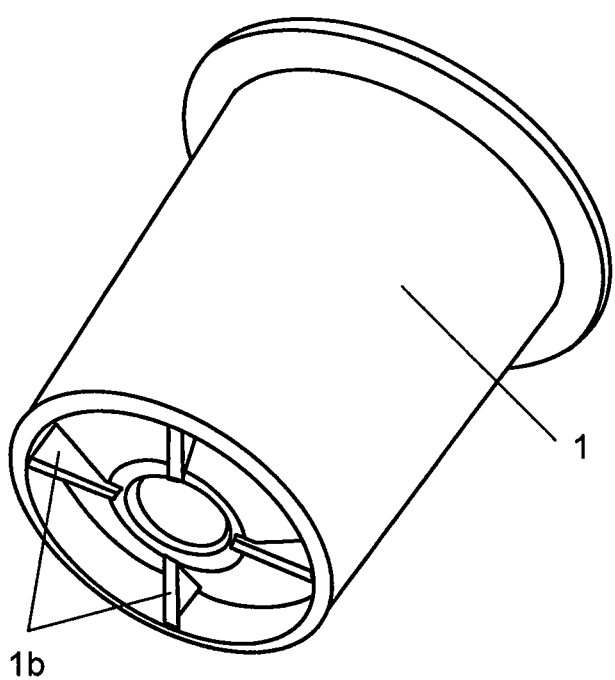
FIG. 14 is a perspective view illustrating a microorganism counting cell according to an exemplary embodiment of the present invention when viewed from below.
Figure 15:
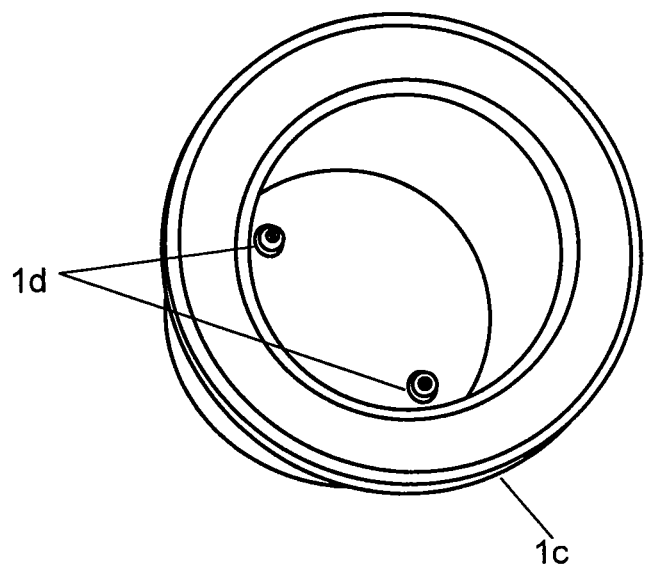
FIG. 15 is a perspective view illustrating a main part of a microorganism counter according to an exemplary embodiment of the present invention.

In rotating vessel 1, four ribs 1b are provided at 90-degree intervals on the outside of the bottom surface of vessel 1 as illustrated in FIG. 14, and driving protrusions 1d of vessel retaining unit is that is provided as a component of a rotation driving unit illustrated in FIGS. 13 and 15 are coupled to the ribs 1b.

Ribs 1b formed outside the bottom surface of vessel 1 constitutes a coupling unit coupled to the driving protrusions 1d of the rotation driving unit that rotates vessel 1.

Because two driving protrusions 1d are provided at 180-degree intervals as illustrated in FIG. 15, the driving protrusions 1d can normally (clockwise) rotate vessel 1 by abutting on rib 1b existing in the rotation direction when vessel retaining unit 1c is normally rotated by motor 1e in FIG. 13 that is provided as a component of the rotation driving unit.

When motor 1e is reversely (counterclockwise) rotated, the driving protrusions 1d can reversely rotate vessel 1 by abutting on rib 1b on the opposite side.

The elution by the normal and reverse rotations will be described in detail.

As illustrated in FIG. 13, for example, motor 1e is normally rotated for 1 second at 7 rps while vessel 1 is retained in vessel retaining unit 1c. Then, motor 1e is reversely rotated for 1 second at 7 rps. The normal and reverse rotation operations are performed for 30 seconds in total.

During the normal and reverse rotation operations, in retaining body 5, as described above, the whole side portion from the lower portion to upper portion of collecting element 4 is retained by abutting on longwall-shaped elution protrusions 7 formed in three side surface bodies 5a from three directions at equal intervals. The whole side portion of collecting element 4 is sequentially scrubbed to longwall-shaped elution protrusions 7 provided on three side surface bodies 5a.

More specifically, the direction in which collecting element 4 scrubs elution protrusion 7 becomes reverse when vessel 1 changes from the normal rotation to the reverse rotation or the reverse rotation to the normal rotation. Therefore, the whole side portion of collecting element 4 is unhardened once by elution protrusions 7, and pure water 9 invades in collecting element 4. When rotated for 1 second at 7 rps, collecting element 4 is scrubbed in the same direction to elution protrusions 7, and the bacteria of collecting element 4 are efficiently eluted along with pure water 9 invading in collecting element 4.

Then, for example, motor 1e is normally rotated for 10 seconds at 7 rps. As described above, the cotton of collecting element 4 is deformed by the continuously normal rotation such that the thickness of the cotton is kept constant. The cotton that becomes the constant thickness by the deformation is scrubbed to and wrung by longwall-shaped elution protrusions 7, and the bacteria remaining finally in collecting element 4 are eluted.

Finally, as illustrated in FIG. 2C, swab portion 4a is scrubbed to elution protrusion 8 and eliminated, and the cotton of collecting element 4 is wrung to an extent that the cotton is wound around rod 3a with the uniform thickness.

As a result, almost all the bacteria collected by collecting element 4 (for example, in the first exemplary embodiment, the bacteria of 85% or more) can be eluted to the outside of collecting element 4 in a short period of time to shorten the elution time of the bacteria (microorganisms).

Then, the number of eluted bacteria is measured.

In the first exemplary embodiment, as illustrated in FIG. 3B, odd-numbered (three) side surface bodies 5a are provided around the side surface of retaining body 5. A width in the horizontal direction of side surface body 5a is larger than a width in the horizontal direction of elution groove 6.

Therefore, collecting element 4 can stably be rotated.

Because odd-numbered (three) side surface bodies 5a are provided around the side surface of retaining body 5, side surface body 5a is disposed opposite elution groove 6 across the rotating shaft of vessel 1 as illustrated in FIG. 3B.

Therefore, during the rotation of retaining body 5, even if collecting element 4 of cotton swab 3 is deviated from the rotating shaft of retaining body 5 to oscillate in the horizontal direction, elution grooves 6 do not exist on both sides in the oscillation direction of collecting element 4 of cotton swab 3. That is, collecting element 4 abuts on side surface body 5a having the width larger than that of elution groove 6 on at least one side in the oscillation direction, and collecting element 4 is returned to the rotating shaft side.

As a result, collecting element 4 can stably be rotated.

The width of elution groove 6 in the circumferential direction is smaller than the thickness of rod 3a of cotton swab 3.

Therefore, collecting element 4 of cotton swab 3 does not fall out to the outside of retaining body 5 through elution groove 6 of retaining body 5.

In the first exemplary embodiment, as illustrated in FIG. 3A, side surface bodies 5a constituting retaining body 5 are vertically disposed on the bottom surface of vessel 1. A space from the outer wall surfaces of side surface bodies 5a constituting retaining body 5 to the inner wall surface of vessel 1 constitutes an elution region where the bacteria is eluted into pure water.

A measurement electrode (not illustrated) of a measurement chip (not illustrated) that measures the number of bacteria can be inserted and dipped in the elution region from the outer wall surfaces of side surface bodies 5a to the inner wall surface of vessel 1. That is, when the number of bacteria is measured using the measurement electrode (not illustrated), because the elution region can be used as the measurement region, convenience is enhanced.

As described above, the microorganism counting cell of the first exemplary embodiment includes bottomed cylindrical vessel 1 that includes upper surface opening 2 and cylindrical retaining body 5 disposed vertically on the bottom surface in vessel 1 and includes the plurality of side surface bodies 5a in which collecting element 4 provided on the lower end portion of cotton swab 3 is inserted from upper surface opening 2, elution protrusions 7 are provided on the interior side surfaces of side surface bodies 5a, and elution grooves 6 each of which pierces retaining body 5 from the inside to the outside are formed among the plurality of side surface bodies 5a. Therefore, the bacteria elution time can be shortened.

That is, in the first exemplary embodiment, because cylindrical retaining body 5 is vertically disposed on the bottom surface in vessel 1, collecting element 4 provided on the lower end portion of cotton swab 3 is inserted from upper surface opening 2 of vessel 1.

At this point, elution protrusions 7 are provided on the interior side surfaces of side surface bodies 5a constituting retaining body 5, and elution grooves 6 that pierce retaining body 5 from the inside to the outside are provided around the side surface of retaining body 5. Therefore, elution protrusions 7 abut on the lower portion to upper portion of collecting element 4, thereby eluting the bacteria from the whole portion from the lower portion to upper portion of collecting element 4. As a result, the elution time of the bacteria (microorganisms) can be shortened.

The eluted bacteria can be eluted to the outside of retaining body 5 through elution grooves 6, namely, to pure water 9 in vessel 1, so that the subsequent measurement can easily be performed.

Accordingly, the microorganism counting cell of the first exemplary embodiment is expected to be widely used as the microorganism counting cell that measures the number of microorganisms existing in the oral cavity or the number of microorganisms adhering to the food.

Second Exemplary Embodiment

Figure 16:
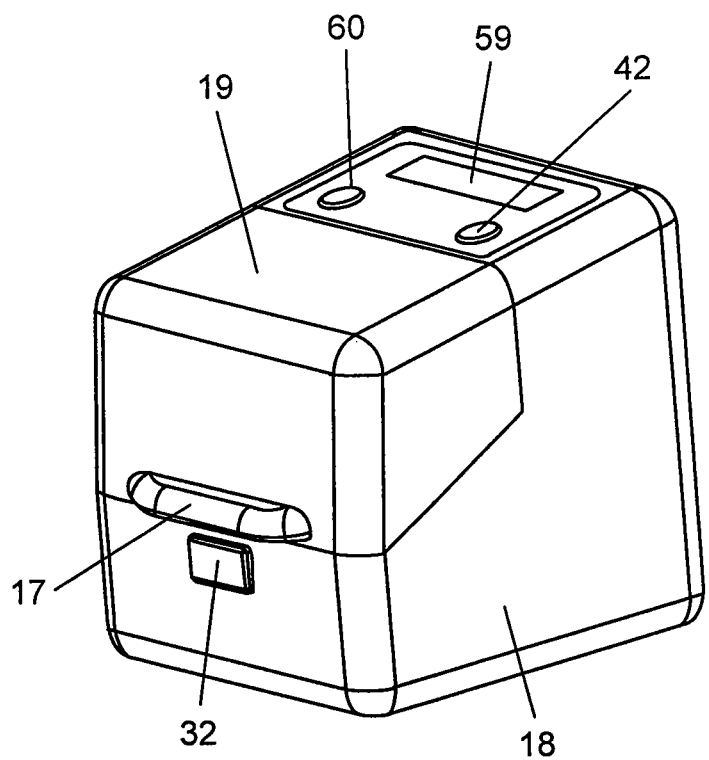
FIG. 16 is a perspective view illustrating a microorganism counter according to an exemplary embodiment of the present invention.
Figure 17:
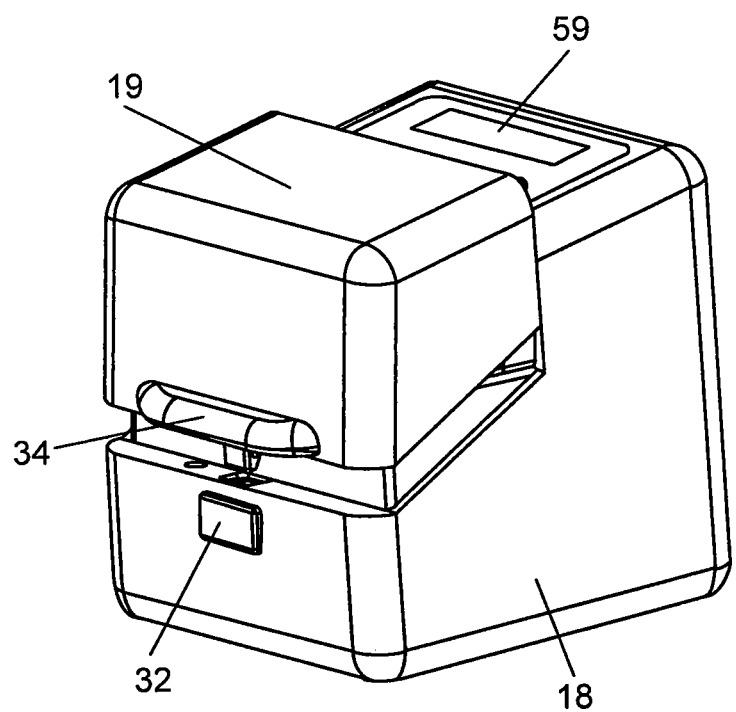
FIG. 17 is a perspective view illustrating a microorganism counter according to an exemplary embodiment of the present invention.
Figure 18:
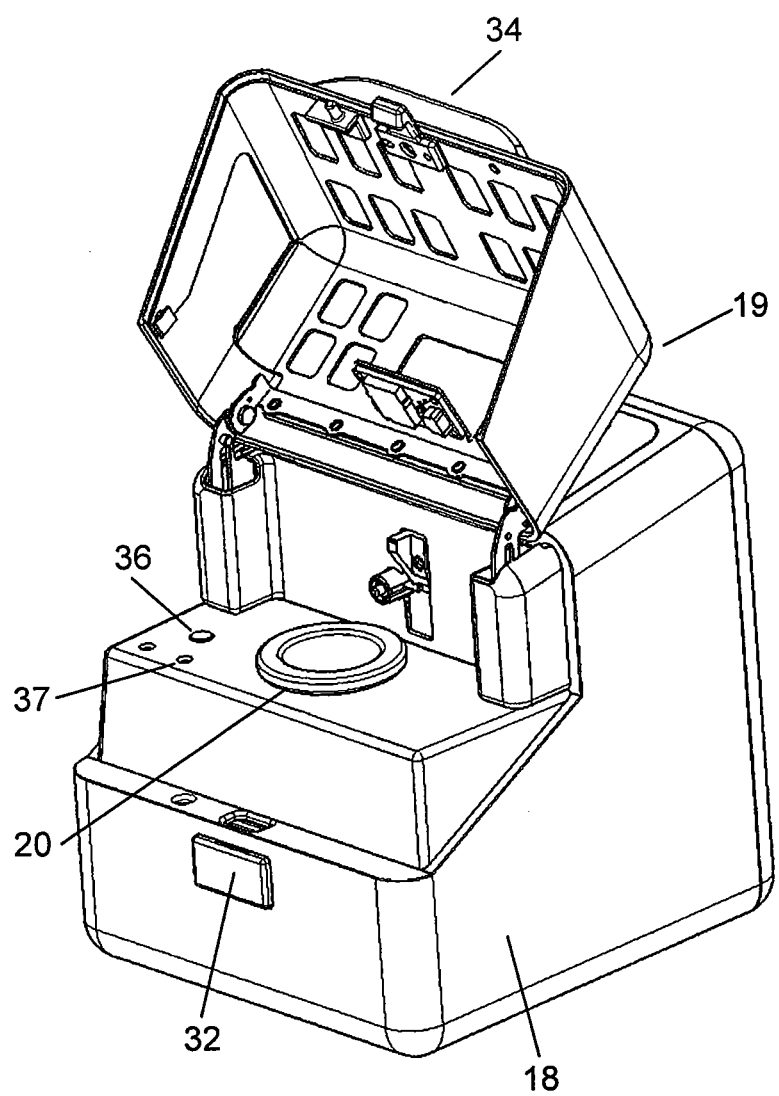
FIG. 18 is a perspective view illustrating a microorganism counter according to an exemplary embodiment of the present invention.
Figure 19:
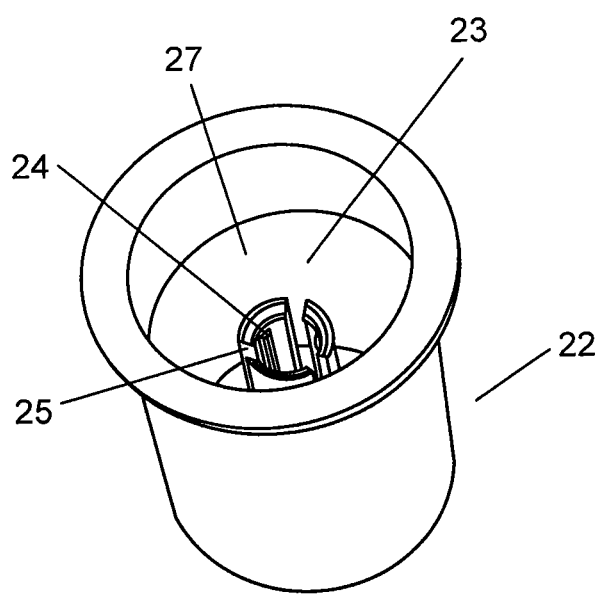
FIG. 19 is a perspective view illustrating a microorganism counting cell according to an exemplary embodiment of the present invention.

As illustrated in FIG. 16, front surface cover 19 in FIGS. 17 and 18 is provided on an openable and closable manner in an upper portion of a front portion of box-shaped body case 18. An opening and closing structure of front surface cover 19 is described in detail later. In releasing front surface cover 19, front surface cover 19 is lifted upward as illustrated in FIGS. 16 and 17, and front surface cover 19 is turned upward as illustrated in FIGS. 17 and 18, thereby performing an opening operation.

As illustrated in FIG. 18, vessel retaining unit 20 is provided on body case 18 on a backside of front surface cover 19, which is exposed by opening front surface cover 19. As can be seen from FIGS. 18 and 25, vessel retaining unit 20 is formed into a bottomed cylindrical shape in which an upper surface is opened. As illustrated in FIG. 26, two driving protrusions 21 are provided so as to face each other at 180-degree intervals in a bottom surface of vessel retaining unit 20.

Figure 25:
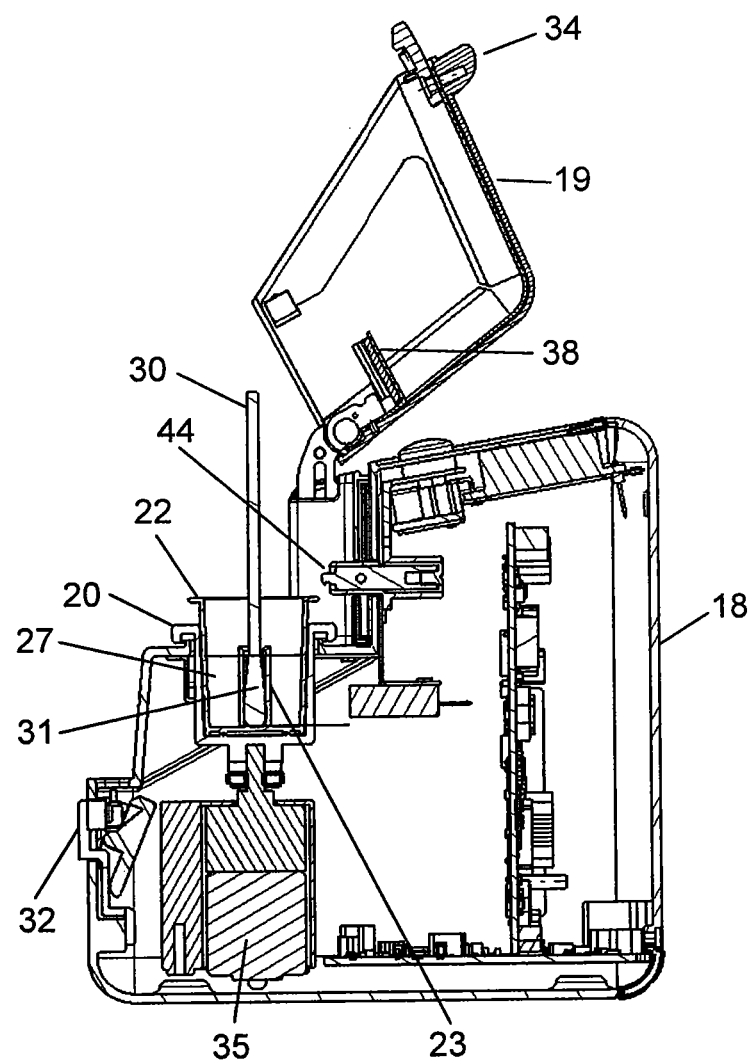
FIG. 25 is a sectional view illustrating a microorganism counter according to an exemplary embodiment of the present invention.
Figure 26:
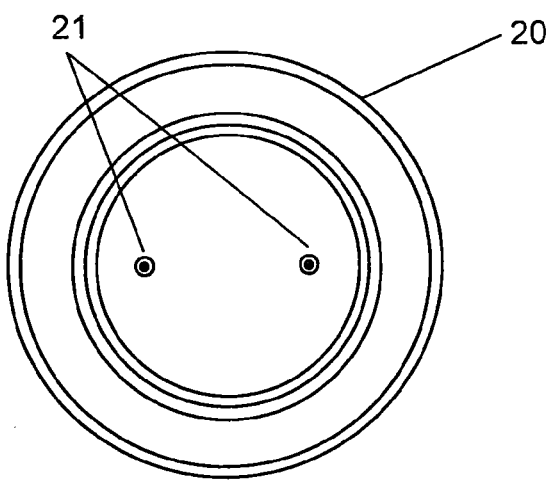
FIG. 26 is a top view illustrating a main part of a microorganism counter according to an exemplary embodiment of the present invention.

As illustrated in FIG. 25, vessel retaining unit 20 retains an outer circumferential surface and a bottom portion of bottomed cylindrical vessel 22 having the opening in the upper surface.

With respect to vessel 22, as can be seen from FIGS. 19 and 21A to 23, cylindrical retaining body 23 is formed on an interior bottom surface of vessel 22, three elution protrusions 24 are vertically formed at 120-degree intervals in an interior side surface of retaining body 23, three elution grooves 25 that pierce retaining body 23 from an inside to an outside are formed at 120-degree intervals in the side surface of retaining body 23 so as to face elution protrusions 24, and three hemispherical elution protrusions 26 are formed at 120-degree intervals in the bottom portion of retaining body 23.

Figure 22:
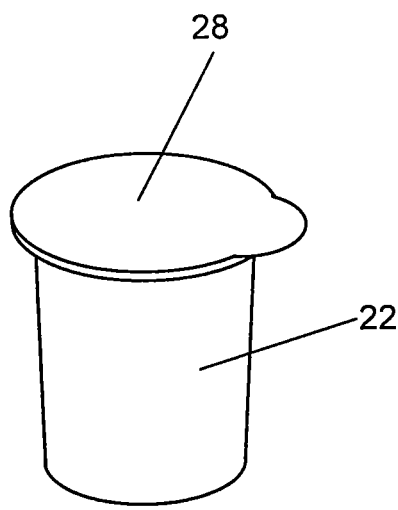
FIG. 22 is a perspective view illustrating a microorganism counting cell according to an exemplary embodiment of the present invention in an unused state.

Pure water 27 which is a liquid into which the microorganisms are eluted is stored in vessel 22, and cover 28 is attached to the upper surface opening of vessel 22 such that pure water 27 does not spill over during conveyance as illustrated in FIG. 22.

Figure 23:
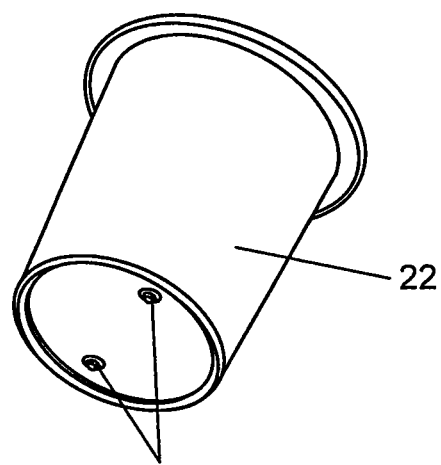
FIG. 23 is a perspective view illustrating a microorganism counting cell according to an exemplary embodiment of the present invention when viewed from below.

As illustrated in FIG. 23, two protrusions 29 that engage driving protrusions 21 of vessel retaining unit 20 are disposed so as to face each other at 180-degree intervals in a lower portion of the bottom surface of vessel 22.

Figures 20A, 20B, 20C:
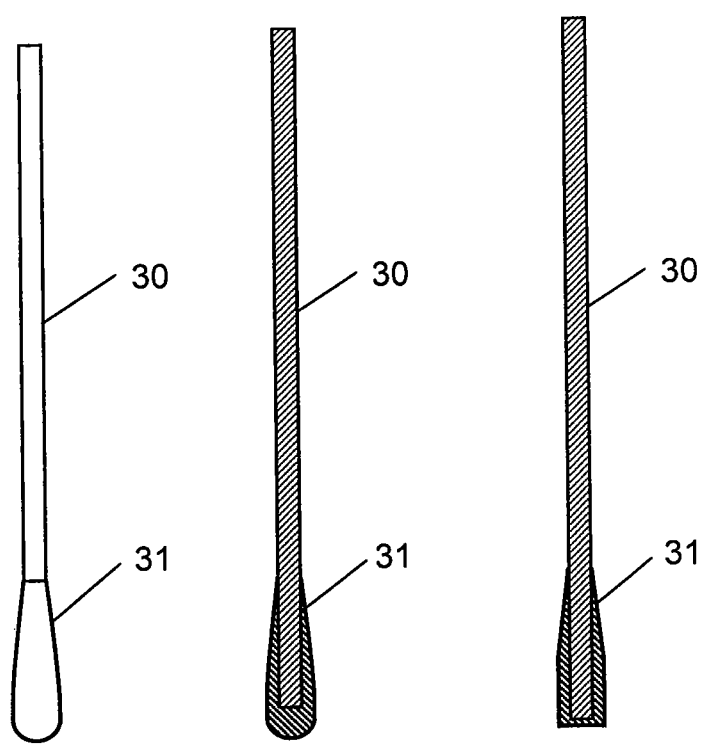
FIG. 20A is a side view illustrating a microorganism collecting tool that is used in use of a microorganism counting cell according to an exemplary embodiment of the present invention.
FIG. 20B is a sectional view illustrating the microorganism collecting tool that is used in use of the microorganism counting cell according to the exemplary embodiment of the present invention.
FIG. 20C is a sectional view illustrating the microorganism collecting tool that is used in use of the microorganism counting cell according to the exemplary embodiment of the present invention.

Collecting element 31 provided at a lower end of rod-shaped microorganism collecting tool (cotton swab) 30 in FIGS. 20A to 20C is inserted from above in retaining body 23 of vessel 22, and the microorganisms are eluted into pure water 27 while the collecting element 31 is inserted in retaining body 23. That is, collecting element 31 of microorganism collecting tool 30 is inserted in the oral cavity, and the microorganisms collected by collecting element 31 are eluted into pure water 27.

The elution of the microorganism into pure water 27 will be described below.

First, manipulation button 32 provided on the lower portion of the front surface of body case 18 in FIG. 16 is pressed in order to start the elution. When manipulation button 32 is pressed, front surface cover 19 is unlocked to slightly lift front surface cover 19 as illustrated in FIG. 17.

Figure 31:
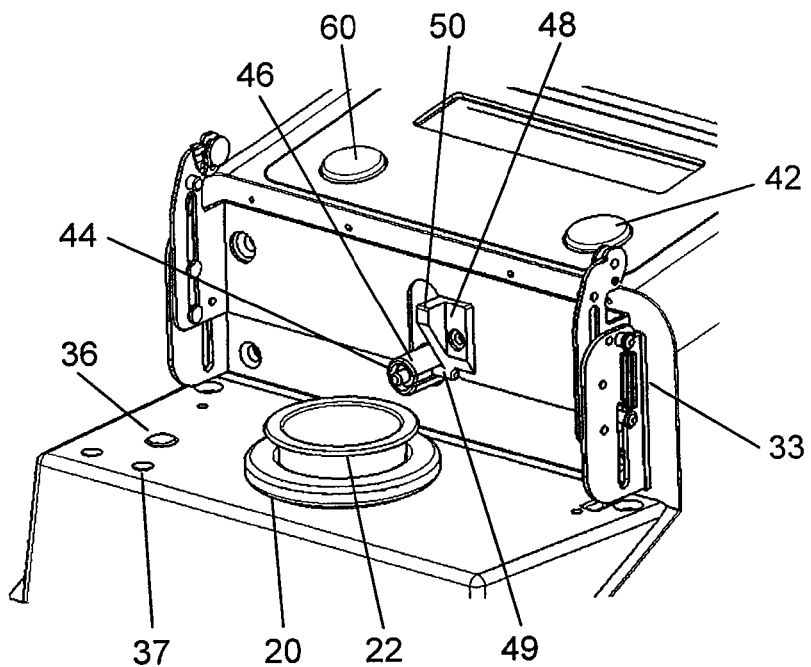
FIG. 31 is a perspective view illustrating a main part of a microorganism counter according to an exemplary embodiment of the present invention.
Figure 32:
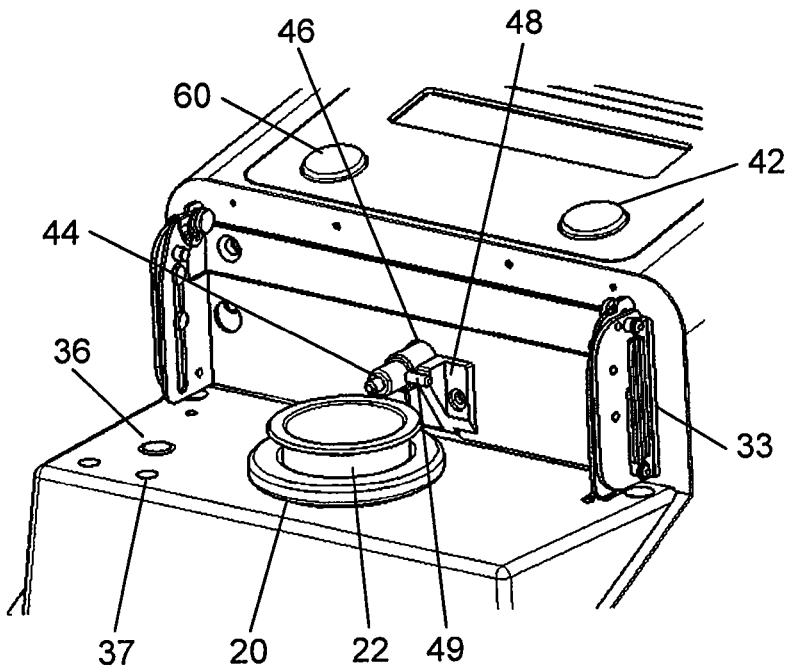
FIG. 32 is a perspective view illustrating a main part of a microorganism counter according to an exemplary embodiment of the present invention.

As illustrated in FIG. 32, springs 33 are mounted on both sides in front surface cover 19 in order to lift front surface cover 19. As described above, when front surface cover 19 is unlocked, the elongated springs 33 in FIG. 32 are returned to an original state in FIG. 31, and front surface cover 19 is lifted by a restoring force at that time. FIGS. 31 and 32 illustrate the later-described operation, and front surface cover 19 is not illustrated for the purpose of easy understanding of an operation to lift front surface cover 19.

After front surface cover 19 is lifted, handle 34 provided at the lower end of the front surface of front surface cover 19 is grasped, front surface cover 19 is lifted and opened, and vessel retaining unit 20 is exposed from body case 18 as illustrated in FIG. 18.

As illustrated in FIG. 22, because cover 28 in FIG. 22 is attached to the upper surface opening of vessel 22, cover 28 is detached from the upper surface opening of vessel 22. In this state, as illustrated in FIGS. 24 and 25, vessel 22 is inserted from below in the upper surface opening of vessel retaining unit 20, whereby the lower portion and outer circumferential portion of vessel 22 are retained by vessel retaining unit 20.

Figure 21A:
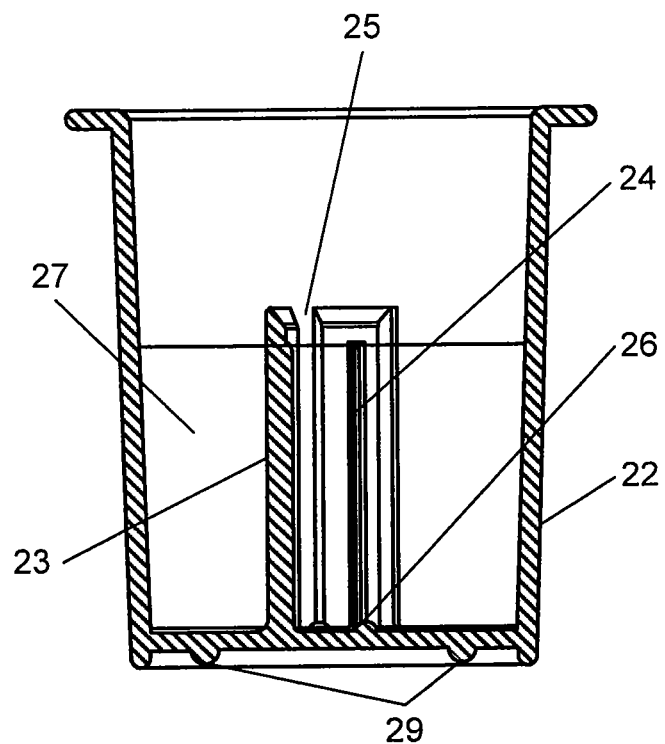
FIG. 21A is a longitudinal sectional view illustrating a microorganism counting cell according to an exemplary embodiment of the present invention.
Figure 21B:
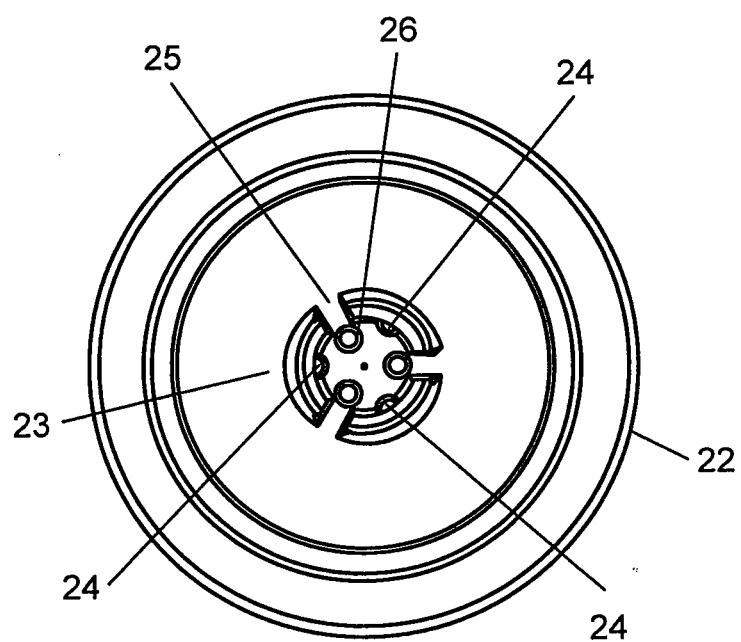
FIG. 21B is a top view illustrating the microorganism counting cell according to the exemplary embodiment of the present invention.

As illustrated in FIGS. 21A and 21B, pure water 27 is stored in vessel 22 retained by vessel retaining unit 20, and collecting element 31 of microorganism collecting tool 30 in FIG. 20 is inserted in pure water 27. Before collecting element 31 of microorganism collecting tool 30 in FIGS. 20A and 20B is inserted in pure water 27, collecting element 31 is inserted in the oral cavity to collect the microorganisms in the oral cavity.

Figure 24:
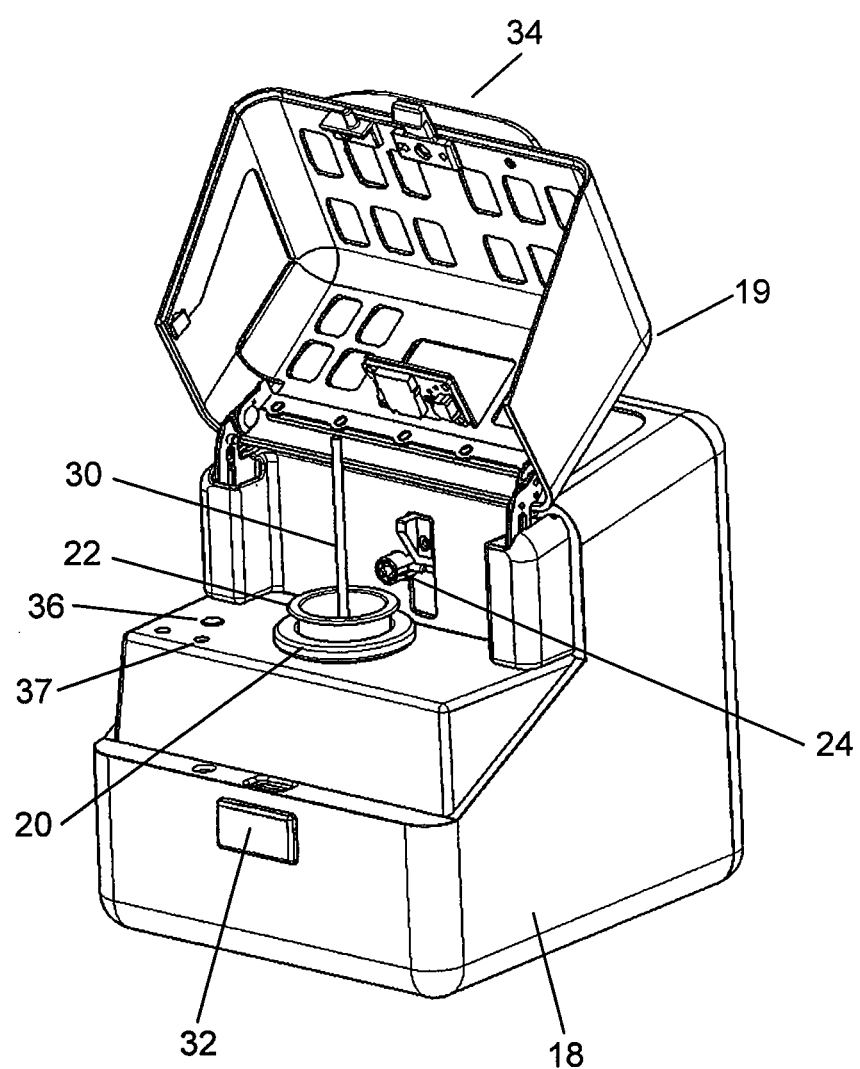
FIG. 24 is a perspective view illustrating a microorganism counter according to an exemplary embodiment of the present invention.

As illustrated in FIGS. 24 and 25, collecting element 31 of microorganism collecting tool 30 is inserted from above in retaining body 23 of vessel 22. At this point, as illustrated in FIGS. 24 and 25, because front surface cover 19 is turned behind the space above the upper surface opening of vessel 22, the work to insert collecting element 31 of microorganism collecting tool 30 in retaining body 23 can extremely easily be performed.

As illustrated in FIGS. 21A and 23, protrusion 29 is provided on the lower portion of the bottom surface of vessel 22. As illustrated in FIG. 26, driving protrusion 21 is provided on the bottom surface of vessel retaining unit 20 that retains vessel 22.

Accordingly, when vessel retaining unit 20 is rotated by motor 35 in FIG. 25, driving protrusion 21 of vessel retaining unit 20 and protrusion 29 in the bottom surface of vessel 22 are engaged with each other to rotate vessel 22.

Switch 36 in FIG. 18 is pressed to rotate motor 35. For example, switch 36 is pressed by a left hand while the upper portion of microorganism collecting tool 30 in FIGS. 24 and 25 is picked by fingers of a right hand.

Because microorganism collecting tool 30 is picked by the fingers of the right hand, microorganism collecting tool 30 is retained in a constant state without the rotation. On the other hand, as described above, vessel 22 is rotated by motor 35 through vessel retaining unit 20 for a set timer time (for example, 10 seconds).

At this point, as illustrated in FIGS. 21A and 21B, a whole circumference of retaining body 23 of vessel 22 is divided into three portions, elution groove 25 exists in the divided portion, and elution protrusion 24 is provided on an inner circumferential surface. Therefore, a pressure is applied from the outside to collecting element 31 of microorganism collecting tool 30 by rotated elution protrusions 24. Therefore, the microorganisms (bacteria) collected by collecting element 31 are extremely effectively eluted into pure water 27 in retaining body 23, and the microorganisms are widely eluted into pure water 27 in vessel 22 through elution groove 25.

Display lamp 37 in FIG. 24 blinks during the elution, and the blinking of display lamp 37 and the rotation of motor 35 are ended when the timer time elapses.

When the elution operation is ended, both the lower portion and the outer circumferential portion of collecting element 31 of microorganism collecting tool 30 are compressed inward as illustrated in FIG. 20C. At this point, the retaining force of retaining body 23 hardly works, and therefore collecting element 31 can easily picked out.

Figure 28:
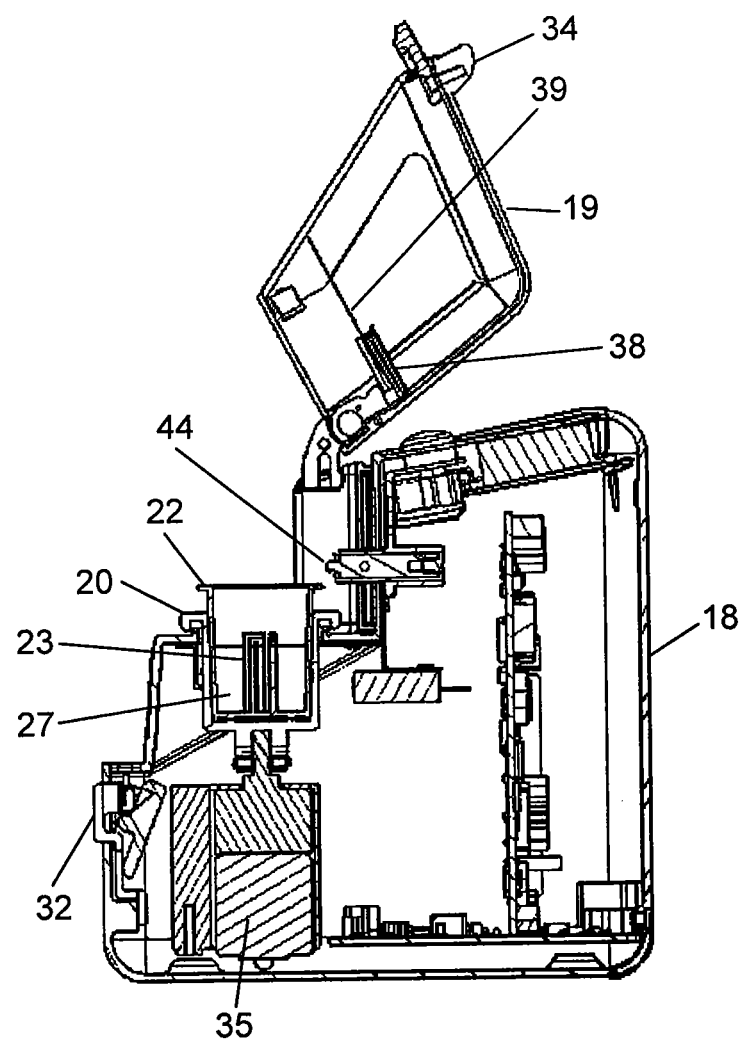
FIG. 28 is a sectional view illustrating a microorganism counter according to an exemplary embodiment of the present invention.

FIG. 28 illustrates the state in which microorganism collecting tool 30 is picked out from vessel 22.

Figure 27:
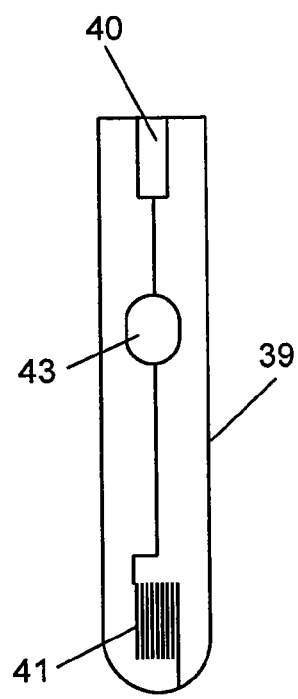
FIG. 27 is a front view illustrating a measurement chip that is used in use of a microorganism counter according to an exemplary embodiment of the present invention.

In the second exemplary embodiment, at this point, measurement chip 39 in FIG. 27 is mounted on measurement chip-retaining unit 38 provided on an inner surface of front surface cover 19.

Specifically, measurement chip 39 is formed into a rectangular plate shape as illustrated in FIG. 27, connection electrode 40 to measurement chip-retaining unit 38 is provided at an upper end of measurement chip 39, and measurement electrode 41 is provided at an lower end of measurement chip 39.

Accordingly, when an intermediate portion of measurement chip 39 is picked to mount connection electrode 40 on measurement chip-retaining unit 38 as illustrated in FIG. 28, the electrical and mechanical connections are established.

The electrode insertion unit includes front surface cover 19 and measurement chip-retaining unit 38. As illustrated in FIG. 28, when front surface cover 19 is lifted and opened, in the electrode insertion unit above vessel 22, a measurement chip insertion port of measurement chip-retaining unit 38 is oriented upward from a horizontal position.

Therefore, connection electrode 40 of measurement chip 39 can easily be mounted on measurement chip-retaining unit 38 while the measurement chip insertion port of measurement chip-retaining unit 38 is visually checked.

Figure 29:
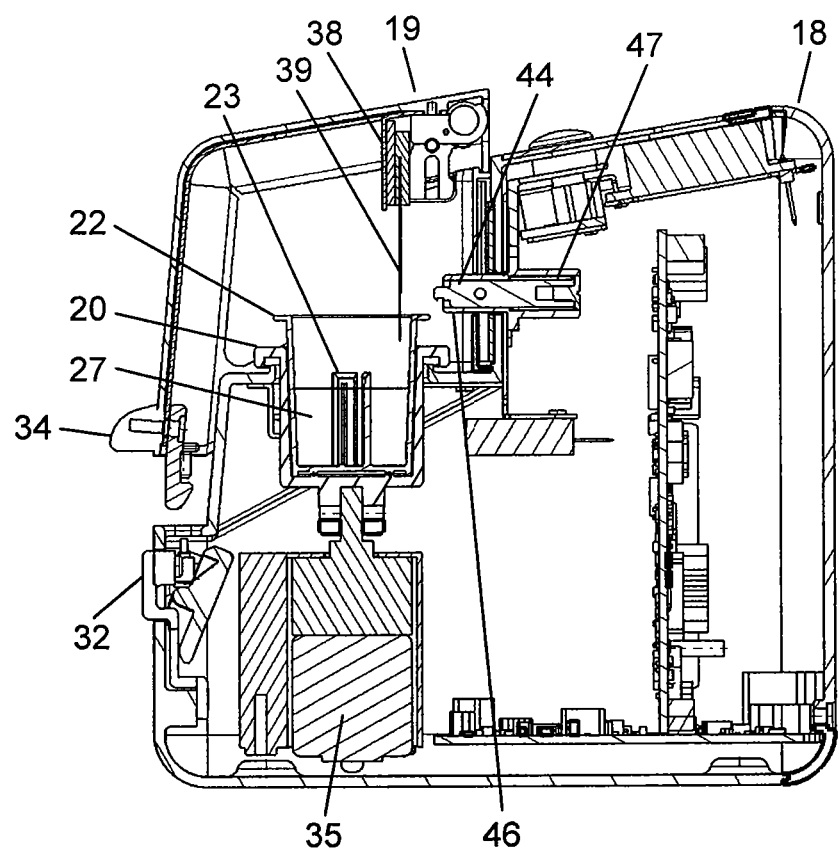
FIG. 29 is a sectional view illustrating a microorganism counter according to an exemplary embodiment of the present invention.

After the state in FIG. 28, when handle 34 is grasped to turn front surface cover 19 frontward and downward to cover the front surface of body case 18 as illustrated in FIG. 29, measurement chip 39 is inserted in the upper surface opening of vessel 22.

Figure 30:
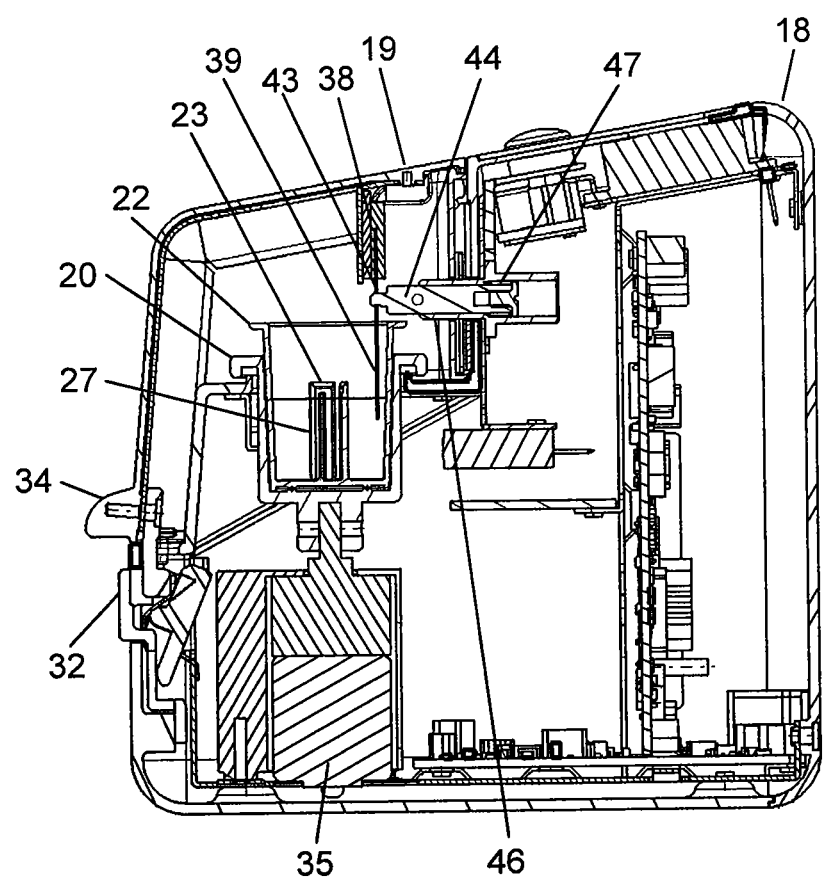
FIG. 30 is a sectional view illustrating a microorganism counter according to an exemplary embodiment of the present invention.

When handle 34 is further lowered as illustrated in FIG. 30, front surface cover 19 is lowered to the state in FIG. 16, and front surface cover 19 is locked. At this point, measurement electrode 41 of measurement chip 39 is dipped in pure water 27 of vessel 22.

That is, measurement start switch 42 in FIG. 16 is pressed while measurement electrode 41 of measurement chip 39 is dipped in pure water 27 of vessel 22 by the electrode insertion unit including front surface cover 19 and measurement chip-retaining unit 38. For example, a 3-MHz voltage is applied to measurement electrode 41 to collect the microorganism eluted in vessel 22 to the portion of measurement electrode 41. At the same time, for example, an 800-kHz voltage is applied to measurement electrode 41 to measure the number of microorganisms.

Because the measurement of the number of microorganisms is well known by a prior literature, the description is simplified for purposes of clarity of description. In the second exemplary embodiment, during the measurement of the number of microorganisms, vessel retaining unit 20 and vessel 22 are rotated by motor 35 to increase an opportunity of bringing the microorganisms diffused widely in vessel 22 close to measurement electrode 41.

In the state in which the number of microorganisms is measured using measurement chip 39, rod-shaped manipulation body 44 constituting a measurement chip separating body is inserted in through-hole 43 in FIG. 27 provided on the intermediate portion of measurement chip 39 as illustrated in FIG. 30.

This point will be described in detail. As is clear from FIG. 29, manipulation body 44 is retreated rearward until measurement chip 39 is completely lowered to vessel 22. As illustrated in FIG. 30, manipulation body 44 protrudes toward the direction of front surface cover 19 before measurement chip 39 is completely lowered to vessel 22.

Figure 33A:
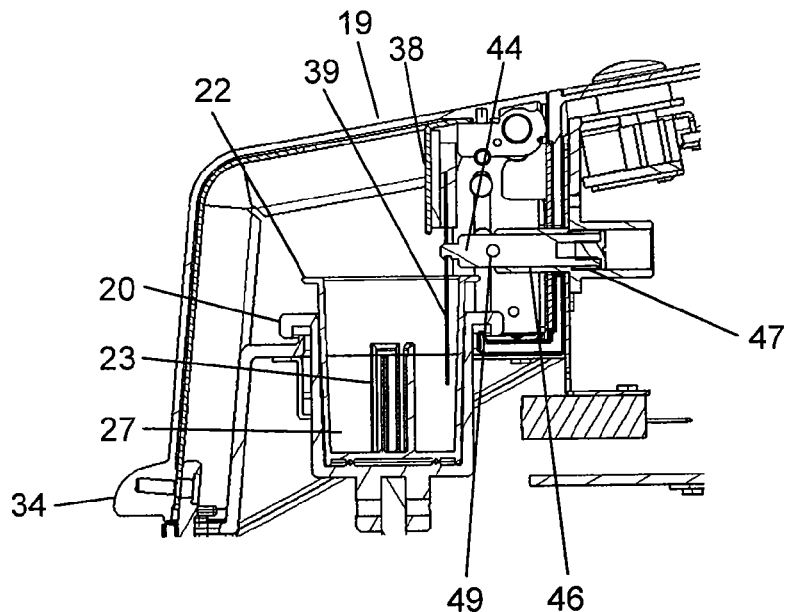
FIG. 33A is a sectional view illustrating a main part of a microorganism counter according to an exemplary embodiment of the present invention.
Figure 33B:
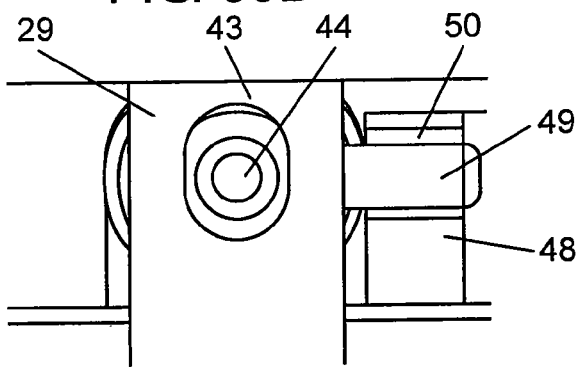
FIG. 33B is an enlarged view illustrating the main part of the microorganism counter according to the exemplary embodiment of the present invention.
Figure 33C:
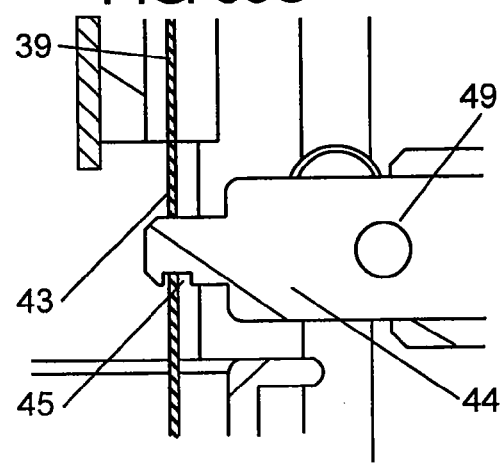
FIG. 33C is a sectional view illustrating the main part of the microorganism counter according to the exemplary embodiment of the present invention.

As can be seen from FIGS. 27, 33B, and 33C, because through-hole 43 made in measurement chip 39 is vertically long, manipulation body 44 can protrude even before measurement chip 39 is completely lowered.

As illustrated in FIG. 33C, hook-shaped engagement portion 45 is provided on a lower surface at a front end of manipulation body 44, and a lower end side of through-hole 43 of measurement chip 39 is engaged with engagement portion 45 when measurement chip 39 is separated.

In the second exemplary embodiment, the number of microorganisms in vessel 22 can be measured in the state in FIG. 30. However, as illustrated in FIG. 28, when front surface cover 19 is opened and closed after the measurement, measurement chip 39 is largely lifted out of vessel 22 along with front surface cover 19, and measurement chip 39 is in the state in which the measurement is already performed in vessel 22.

That is, as illustrated in FIG. 28, when measurement chip 39 is lifted along with front surface cover 19 after the measurement, undesirably pure water 27 containing the microorganisms adhering during the measurement is carelessly spattered or drops onto the front portion or lower portion of front surface cover 19. Therefore, in the second exemplary embodiment, manipulation body 44 constituting the measurement chip separating body is provided as described above.

This point will further specifically be described in detail. When the number of microorganisms is measured using measurement chip 39, namely, when measurement electrode 41 of measurement chip 39 is dipped in pure water 27 as illustrated in FIG. 30, manipulation body 44 is already protruded in through-hole 43 of measurement chip 39.

The mechanism in FIGS. 31 and 32 causes manipulation body 44 to protrude from the state in FIG. 29 to the state in FIG. 30, and causes manipulation body 44 to retreat from the state in FIG. 30 to the state in FIG. 29. Manipulation body 44 is slidably provided on cylindrical guide tube 46, and guide tube 46 is fixed to body case 18. In guide tube 46, manipulation body 44 is always biased in the rear direction opposite to front surface cover 19 by spring 47 in FIG. 29. FIGS. 29 and 31 illustrate this state.

When front surface cover 19 is further pushed down from the state in FIG. 29 to the state in FIG. 30 to dip measurement electrode 41 of measurement chip 39 in pure water 27, cam plate 48 is lowered from the state in FIG. 31 to the state in FIG. 32 in conjunction with the lowering operation of front surface cover 19, thereby causing manipulation body 44 to protrude onto the side of measurement chip 39. That is, because the upper portion of cam plate 48 protrudes onto the side of front surface cover 19 (the side of measurement chip 39) compared with the lower portion of cam plate 48, the upper portion of cam plate 48 pushes manipulation pin 49 of manipulation body 44 onto the side of front surface cover 19 (the side of measurement chip 39) as cam plate 48 is lowered. As a result, manipulation body 44 invades in through-hole 43 of measurement chip 39 as illustrated in FIG. 33.

When manipulation body 44 protrudes in the front direction which is the side of front surface cover 19, spring 47 is compressed as illustrated in FIGS. 30 and 33.

Figure 35A:
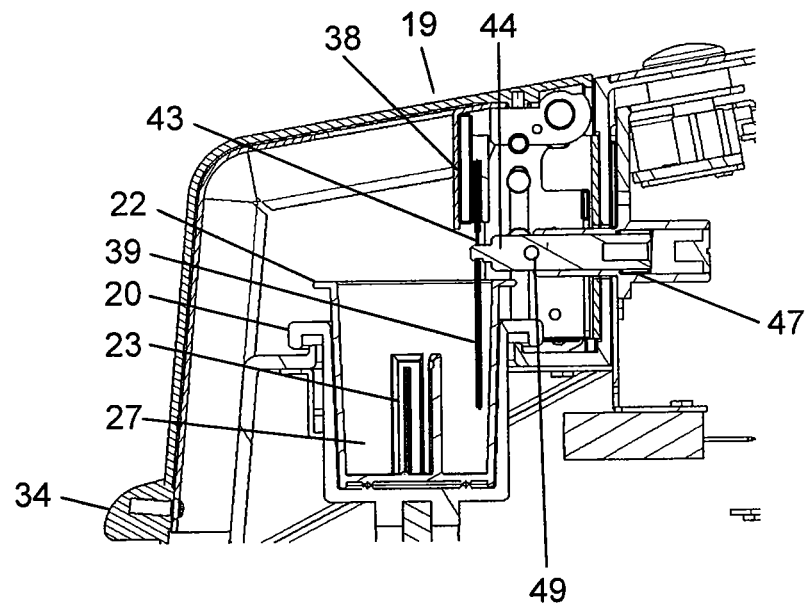
FIG. 35A is a sectional view illustrating a main part of a microorganism counter according to an exemplary embodiment of the present invention.
Figure 35B:
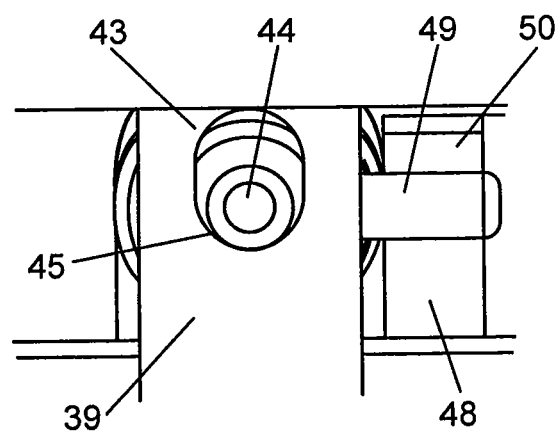
FIG. 35B is an enlarged view illustrating the main part of the microorganism counter according to the exemplary embodiment of the present invention.

FIGS. 35A and 35B illustrate the state immediately after front surface cover 19 is lifted by the restoring force of spring 33 in FIG. 32 after the measurement. At this point, because protruded flat surface 50 in FIG. 33B exists in the upper end portion of the cam plate 48, manipulation body 44 does not retreat but is maintained in a given position immediately after front surface cover 19 is lifted.

However, because connection electrode 40 in the upper end portion of measurement chip 39 is retained by measurement chip-retaining unit 38, connection electrode 40 is slightly lifted as front surface cover 19 is slightly lifted as illustrated in FIG. 35A. As a result, hook-shaped engagement portion 45 of manipulation body 44 is engaged with the lower end portion of through-hole 43 of measurement chip 39 as illustrated in FIG. 35B.

Figure 36A:
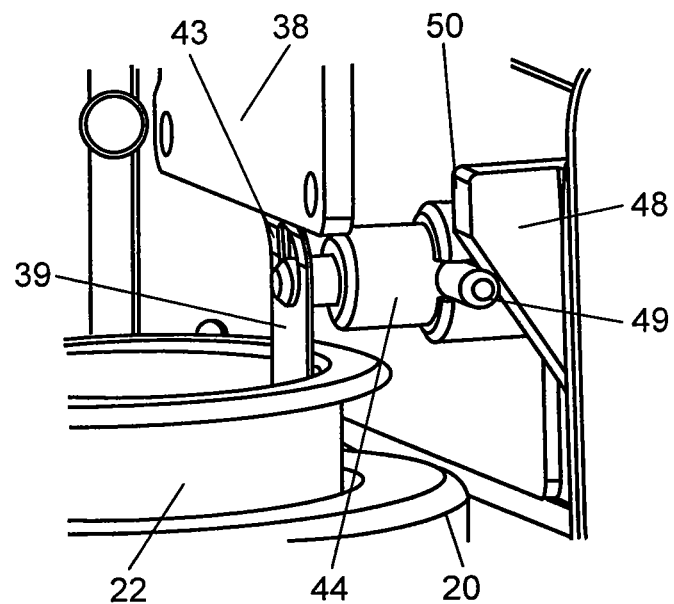
FIG. 36A is a perspective view illustrating a main part of a microorganism counter according to an exemplary embodiment of the present invention.
Figure 36B:
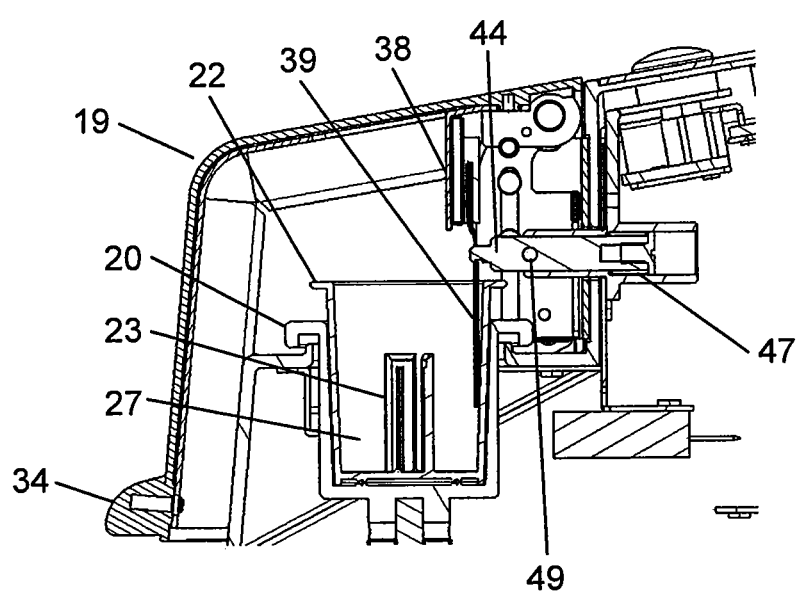
FIG. 36B is a sectional view illustrating the main part of the microorganism counter according to the exemplary embodiment of the present invention.

FIGS. 36A and 36B illustrate a moment in which front surface cover 19 is further lifted from this state. As illustrated in FIG. 36A, manipulation pin 49 of manipulation body 44 is separated from flat surface 50 of cam plate 48 by lifting front surface cover 19, and moves to an inclination portion of cam plate 48.

As a result, manipulation body 44 retreats rearward by the restoring force of spring 47, whereby a portion below through-hole 43 of flexible measurement chip 39 is moved rearward. Then, as illustrated in FIG. 36B, the portion is pressed against the inner wall surface of vessel 22.

As described above, because hook-shaped engagement portion 45 is provided at the front end of manipulation body 44, the portion below the through-hole 43 of measurement chip 39 can stably be pulled rearward as illustrated in FIG. 36B.

On the other hand, a portion above through-hole 43 of measurement chip 39 is retained by measurement chip-retaining unit 38, the portion above through-hole 43 of measurement chip 39 is inclined forward compared with the portion below through-hole 43 of measurement chip 39.

Figure 37:
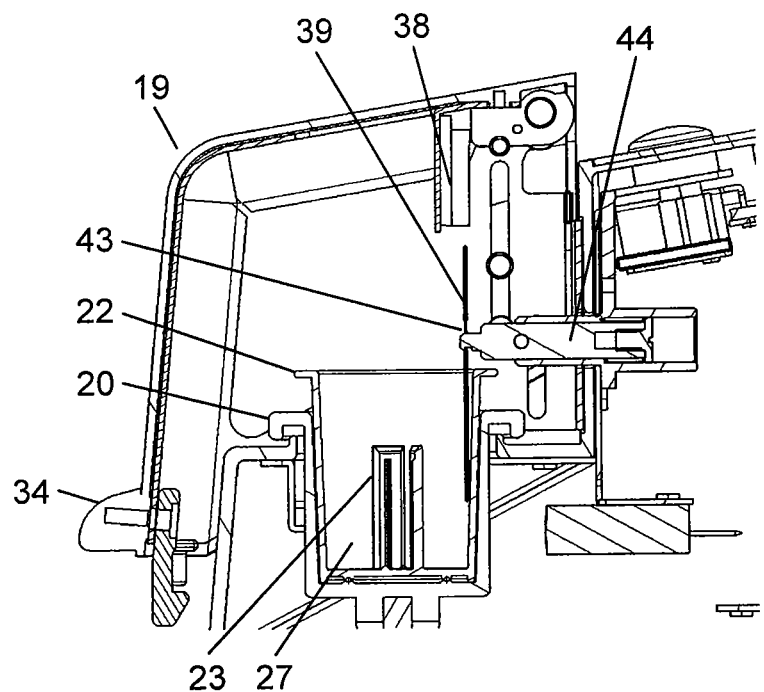
FIG. 37 is a sectional view illustrating a microorganism counter according to an exemplary embodiment of the present invention.

FIG. 37 illustrates the state in which front surface cover 19 is further lifted. When front surface cover 19 is lifted to the position in FIG. 37, connection electrode 40 of measurement chip 39 is separated from measurement chip-retaining unit 38. In this state, front surface cover 19 is opened upward by handle 34 as illustrated in FIG. 28, and then measurement chip 39 is picked out from vessel 22.

In the second exemplary embodiment, one of the features is that, even if front surface cover 19 is opened, measurement chip 39 is not lifted out of vessel 22 in conjunction with the opening operation.

Therefore, even if the opening operation of front surface cover 19 is performed, pure water 27 containing the microorganisms adhering during the measurement is not carelessly spattered or does not drop onto the front portion or lower portion of front surface cover 19, so that a desirable situation is obtained from a hygiene viewpoint.

In the second exemplary embodiment, as illustrated in FIG. 37, in order to pick out measurement chip 39 retained by manipulation body 44, when connection electrode 40 in the upper end portion of measurement chip 39 is picked to slightly press connection electrode 40 in the inward direction of vessel 22 located below, measurement chip 39 is disengaged with through-hole 43 of engagement portion 45 of manipulation body 44, so that measurement chip 39 can easily be picked out to the outside of vessel 22.

Additionally, because the upper end portion of connection electrode 40 that is used to pick out measurement chip 39 is not dipped in pure water 27 of vessel 22, a trouble is not generated from the hygiene viewpoint even if the upper end portion of connection electrode 40 is picked.

Figure 38A:
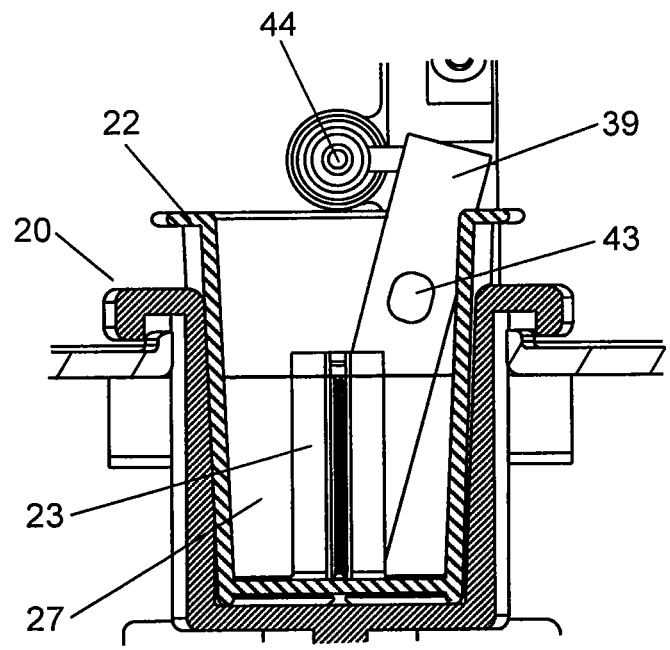
FIG. 38A is a sectional view illustrating a main part of a microorganism counter according to an exemplary embodiment of the present invention.
Figure 38B:
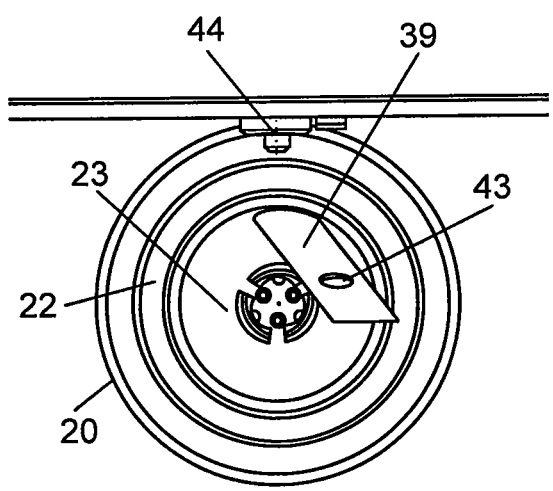
FIG. 38B is a top view illustrating the main part of the microorganism counter according to the exemplary embodiment of the present invention.

FIGS. 38A and 38B illustrate the state in which measurement chip 39 mistakenly drops during the work to pick out measurement chip 39. As illustrated in FIGS. 38A and 38B, because dropped measurement chip 39 is retained in vessel 22, measurement chip 39 does not carelessly drop in a floor, and the trouble is not generated from the hygiene viewpoint.

In the second exemplary embodiment, a length of measurement chip 39 is larger than a depth of vessel 22. Therefore, even if measurement chip 39 drops in vessel 22 as illustrated in FIGS. 38A and 38B, measurement chip 39 can easily be picked out and discarded without touching pure water 27 in vessel 22 by picking the upper end portion of measurement chip 39.

Figure 34:
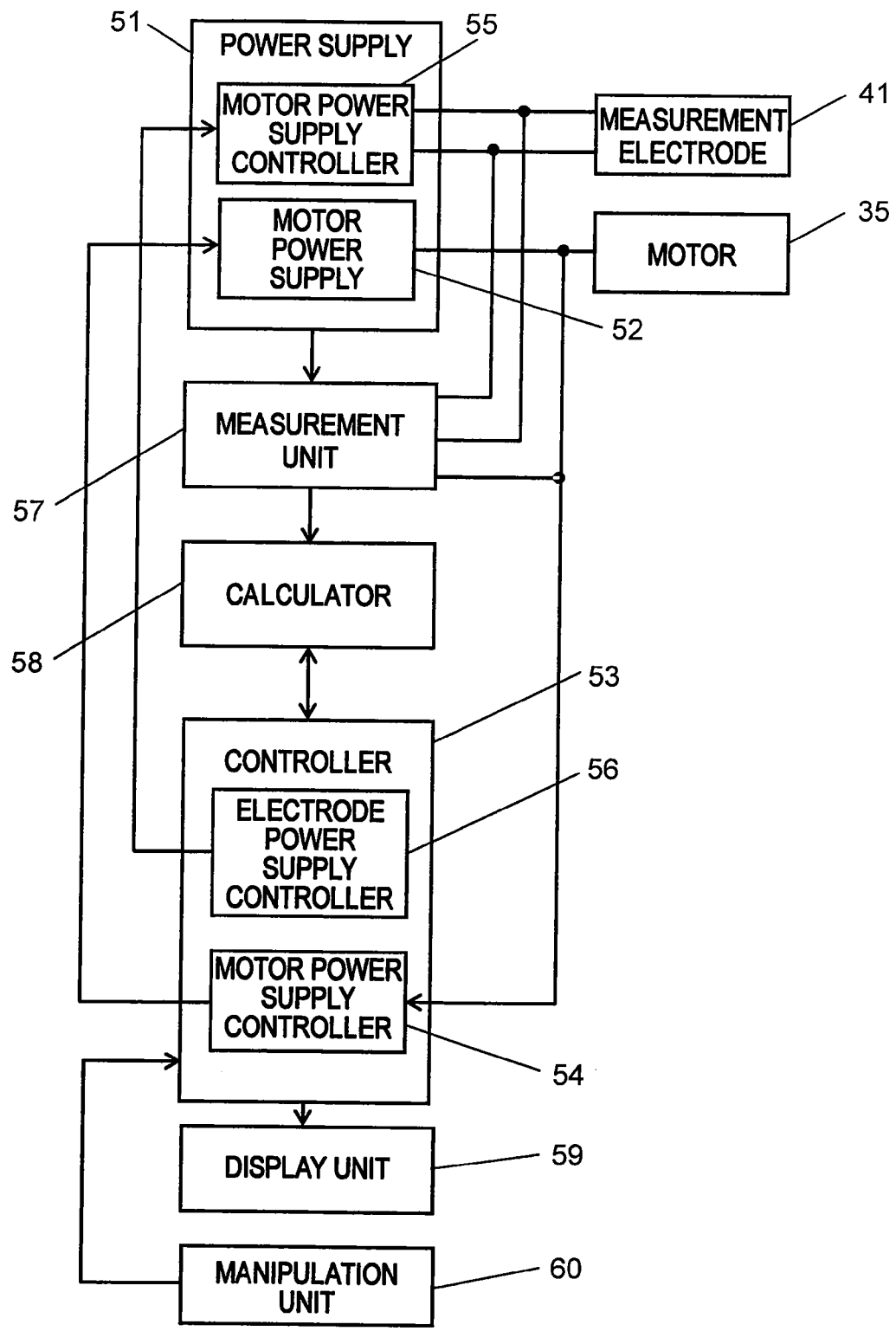
FIG. 34 is a control block diagram illustrating a microorganism counter according to an exemplary embodiment of the present invention.

FIG. 34 illustrates a control block diagram for performing the above operations.

As illustrated in FIG. 34, motor 35 is connected to motor power supply 52 of power supply 51, and motor power supply 52 is connected to motor power supply controller 54 of controller 53. Electrode power supply 55 of power supply 51 is connected to measurement electrode 41, and electrode power supply 55 is connected to electrode power supply controller 56.

That is, electrode power supply 55 applies the 3-MHz voltage and the 800-kHz voltage to measurement electrode 41, and measurement unit 57 and calculator 58, which are connected to measurement electrode 41, simultaneously measure the number of microorganisms. A measurement value is displayed on display unit 59 provided at the back of front surface cover 19.

Manipulation unit 60 illustrated below display unit 59 in FIG. 34 is a power supply manipulation unit. Although switch 36, display lamp 37, and measurement start switch 42 in FIG. 18 are not illustrated in FIG. 34, switch 36, display lamp 37, and measurement start switch 42 are connected to controller 53.

As described above, the microorganism counter of the second exemplary embodiment includes: vessel retaining unit 20 that retains bottomed cylindrical vessel 22 including the upper surface opening with the opening oriented upward; motor (rotation driving unit) 35 that rotates vessel 22 retained by vessel retaining unit 20 around a vertically rotating shaft; measurement chip-retaining unit 38 (constituting the electrode insertion unit) that inserts measurement chip 39 in vessel 22 through the opening from above vessel 22 retained by vessel retaining unit 20; and measurement unit 57 that measures the microorganism using measurement electrode 41 of measurement chip 39 that is inserted in vessel 22 by the electrode insertion unit, wherein measurement chip 39 is detachably mounted on measurement chip-retaining unit 38 (constituting the electrode insertion unit), and manipulation body 44 (constituting the measurement chip separating body) that retains measurement chip 39 while measurement chip 39 is inserted in vessel 22 is provided. Therefore, reduction of measurement cost can be achieved.

That is, in the microorganism counter of the second exemplary embodiment, the electrode insertion unit that inserts measurement chip 39 in vessel 22 through the opening from above vessel 22 retained by vessel retaining unit 20 is provided. Therefore, the simple vessel having the bottomed cylindrical shape in which the opening is provided on the upper surface may be used as vessel 22, so that therefore production cost of vessel 22 can be reduced to achieve the reduction of the measurement cost.

In the secondary exemplary embodiment, measurement chip 39 is detachably mounted on measurement chip-retaining unit 38 (constituting the electrode insertion unit), and manipulation body 44 (constituting the measurement chip separating body) that retains measurement chip 39 while measurement chip 39 is inserted in vessel 22 is provided. Therefore, measurement chip 39 is not spattered or does not drop in discharging measurement chip 39 after the measurement. As a result, the hygiene effect can be enhanced.

Figure 39:
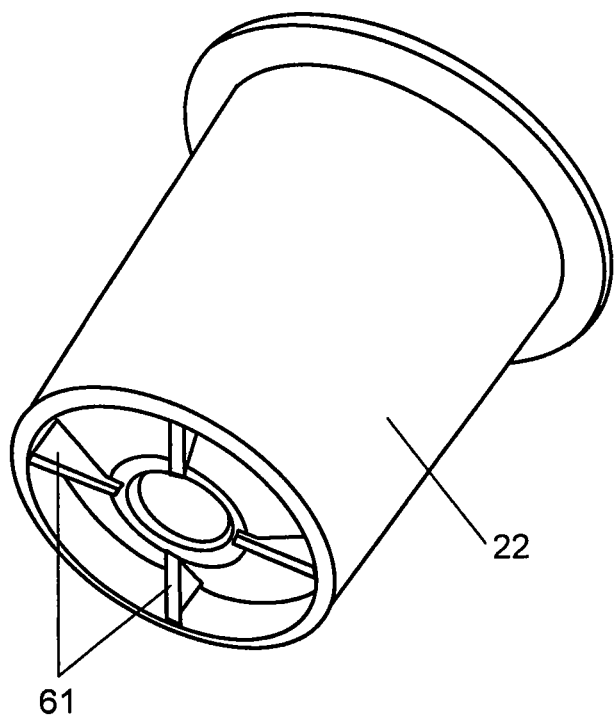
FIG. 39 is a perspective view illustrating a microorganism counting cell according to an exemplary embodiment of the present invention when viewed from below.

In the second exemplary embodiment, when vessel 22 is rotated, four ribs 61 are provided at 90-degree intervals outside the bottom surface of vessel 22 as illustrated in FIG. 39, and driving protrusions 21 in FIG. 26 may be coupled to ribs 61.

As illustrated in FIG. 26, because two driving protrusions 21 are provided at 180-degree intervals, when vessel retaining unit 20 is rotated by motor 35, driving protrusions 21 can abut on ribs 61 existing in the rotating direction to rotate vessel 22. When motor 35 is reversely rotated, driving protrusions 21 can abut on ribs 61 on the reverse rotation side to reversely rotate vessel 22.

In the second exemplary embodiment, as illustrated in FIG. 33C, hook-shaped engagement portion 45 is provided on the lower surface at the front end of manipulation body 44, and the lower end side of through-hole 43 of measurement chip 39 is engaged with engagement portion 45 when measurement chip 39 is separated. Alternatively, a structure in which hook-shaped engagement portion 45 is not provided at the front end of manipulation body 44 may be adopted as illustrated in FIG. 40.

Figure 40:
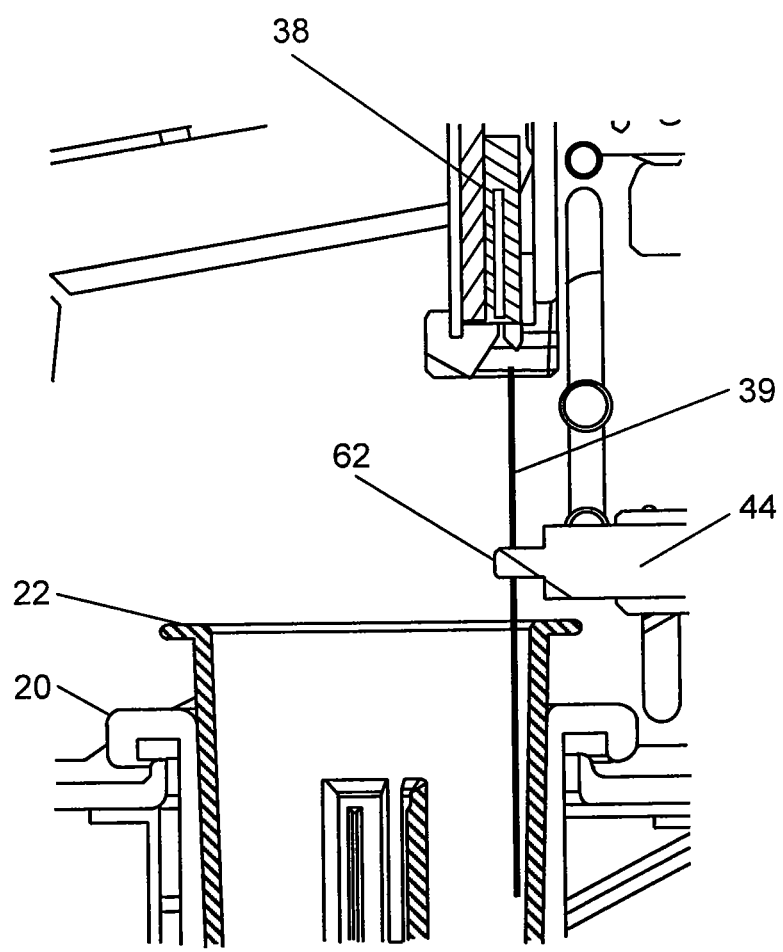
FIG. 40 is a sectional view illustrating a main part of a microorganism counter according to an exemplary embodiment of the present invention.

When hook-shaped engagement portion 45 is not provided, front end portion 62 of manipulation body 44 invades in through-hole 43 of measurement chip 39 as illustrated in FIG. 40 while front surface cover 19 is closed as illustrated in FIG. 30.

In opening front surface cover 19 after the measurement, the lower end of through-hole 43 of measurement chip 39 is engaged with front end portion 62 of manipulation body 44, and therefore measurement chip 39 is separated from measurement chip-retaining unit 38. In opening front surface cover 19, when manipulation body 44 is pulled rearward (right side) in FIG. 40 while measurement chip 39 is separated from measurement chip-retaining unit 38, front end portion 62 of manipulation body 44 is extracted from through-hole 43 of measurement chip 39.

Therefore, measurement chip 39 drops in vessel 22.

Accordingly, when front surface cover 19 is opened after the measurement, measurement chip 39 is taken out from vessel retaining unit 20 while stored in vessel 22, and discarded as a medical waste.

Third Exemplary Embodiment

In the second exemplary embodiment, the elution of the microorganisms into pure water 27 is performed such that, while front surface cover 19 is opened, the upper portion of microorganism collecting tool 30 is picked by the fingers of the right hand, for example, to rotate vessel 22 through vessel retaining unit 20 using motor 35.

On the other hand, in a configuration of a third exemplary embodiment, when front surface cover 19 is closed, the upper portion of microorganism collecting tool 30 is retained by the microorganism collecting tool retaining unit (not illustrated) provided on the inner surface side of front surface cover 19. According to the configuration of the third exemplary embodiment, the operation to pick the upper portion of microorganism collecting tool 30 between the fingers is eliminated during the elution of the microorganisms into pure water 27.

Specifically, when manipulation button 32 in FIG. 16 provided on the lower portion of the front surface of body case 18 is pressed, front surface cover 19 is unlocked and slightly lifted front surface cover 19 as illustrated in FIG. 17.

As illustrated in FIG. 32, springs 33 are mounted on both sides in front surface cover 19 in order to lift front surface cover 19. As described above, when front surface cover 19 is unlocked, the elongated springs 33 in FIG. 32 are returned to the original state in FIG. 31, and front surface cover 19 is lifted by the restoring force at that time. FIGS. 31 and 32 illustrate the later-described operation, and front surface cover 19 is not illustrated for the purpose of easy understanding of an operation to lift front surface cover 19.

After front surface cover 19 is lifted, handle 34 provided at the lower end of the front surface of front surface cover 19 is grasped, front surface cover 19 is lifted and opened, and vessel retaining unit 20 is exposed from body case 18 as illustrated in FIG. 18.

As illustrated in FIG. 22, because cover 28 is attached to the upper surface opening of vessel 22, cover 28 is detached from the upper surface opening of vessel 22. At this point, as illustrated in FIGS. 24 and 25, vessel 22 is inserted from below in the upper surface opening of vessel retaining unit 20, whereby the lower portion and outer circumferential portion of vessel 22 are retained by vessel retaining unit 20.

As illustrated in FIGS. 21A and 21B, pure water 27 is stored in vessel 22 retained by vessel retaining unit 20, and collecting element 31 of microorganism collecting tool 30 in FIGS. 20A and 20B is inserted in pure water 27. Before collecting element 31 of microorganism collecting tool 30 in FIGS. 20A and 20B is inserted in pure water 27, collecting element 31 is inserted in the oral cavity to collect the microorganisms in the oral cavity.

As illustrated in FIGS. 24 and 25, collecting element 31 of microorganism collecting tool 30 is inserted from above in retaining body 23. At this point, as illustrated in FIGS. 24 and 25, because front surface cover 19 is turned behind the space above the upper surface opening of vessel 22, the work to insert collecting element 31 of microorganism collecting tool 30 in retaining body 23 can extremely easily be performed.

As illustrated in FIGS. 21 and 23, protrusion 29 is provided on the lower portion of the bottom surface of vessel 22. As illustrated in FIG. 26, driving protrusion 21 is provided on the bottom surface of vessel retaining unit 20 that retains vessel 22.

In the third exemplary embodiment, at this point, measurement chip 39 in FIG. 27 is mounted on measurement chip-retaining unit 38 provided on the inner surface of front surface cover 19.

Specifically, measurement chip 39 is formed into a rectangular plate shape as illustrated in FIG. 27, connection electrode 40 to measurement chip-retaining unit 38 is provided at an upper end of measurement chip 39, and measurement electrode 41 is provided at an lower end of measurement chip 39.

Accordingly, when an intermediate portion of measurement chip 39 is picked to mount connection electrode 40 on measurement chip-retaining unit 38 as illustrated in FIG. 28, the electrical and mechanical connections are established.

Specifically, the electrode insertion unit includes front surface cover 19 and measurement chip-retaining unit 38. As illustrated in FIG. 28, when front surface cover 19 is lifted and opened, in the electrode insertion unit above vessel 22, a measurement chip insertion port of measurement chip-retaining unit 38 is oriented upward from a horizontal position.

Therefore, connection electrode 40 of measurement chip 39 can easily be mounted on measurement chip-retaining unit 38 while the measurement chip insertion port of measurement chip-retaining unit 38 is visually checked.

After the state in FIG. 28, when handle 34 is grasped to turn front surface cover 19 frontward and downward to cover the front surface of body case 18 as illustrated in FIG. 29, measurement chip 39 is inserted in the upper surface opening of vessel 22. When handle 34 is further lowered as illustrated in FIG. 30, front surface cover 19 is lowered to the state in FIG. 16, and the front surface cover 19 is locked. At this point, measurement electrode 41 of measurement chip 39 is dipped in pure water 27 of vessel 22.

When front surface cover 19 is lowered to the state in FIG. 16, the upper portion of microorganism collecting tool 30 is retained by the microorganism collecting tool retaining unit (not illustrated) provided on the inner surface side of front surface cover 19. According to the configuration of the third exemplary embodiment, unlike the second exemplary embodiment, the operation to pick the upper portion of microorganism collecting tool 30 between the fingers is eliminated during the elution of the microorganisms into pure water 27.

Front surface cover 19 is lowered to the state in FIG. 16, measurement electrode 41 of measurement chip 39 is dipped in pure water 27 of vessel 22, and the upper portion of microorganism collecting tool 30 is retained by the microorganism collecting tool retaining unit (not illustrated). At this point, measurement start switch 42 in FIG. 16 is pressed.

Therefore, vessel retaining unit 20 is rotated by motor 35 in FIG. 25, and driving protrusion 21 and protrusion 29 are engaged with each other, thereby rotating vessel 22.

Because the upper portion of microorganism collecting tool 30 is retained by the microorganism collecting tool retaining unit (not illustrated), microorganism collecting tool 30 is not rotated but maintained in a constant state. At this point, as described above, vessel 22 is rotated by motor 35 through vessel retaining unit 20 for a set timer time (for example, 10 seconds).

At this point, the whole circumference of retaining body 23 of vessel 22 is divided into three portions, elution groove 25 exists in the divided portion, and elution protrusion 24 is provided on the inner circumferential surface. Therefore, the pressure is applied from the outside to collecting element 31 of microorganism collecting tool 30 by rotated elution protrusions 24. Therefore, the microorganisms (bacteria) collected by collecting element 31 are extremely effectively eluted into pure water 27 in retaining body 23, and the next moment, the microorganisms are widely eluted into pure water 27 in vessel 22 through elution groove 25.

Then, for example, a 3-MHz voltage is applied to measurement electrode 41 to collect the microorganism eluted in vessel 22 to the portion of measurement electrode 41. At the same time, for example, an 800-kHz voltage is applied to measurement electrode 41 to measure the number of microorganisms.

Because the measurement of the number of microorganisms is well known by the prior literature, the description is simplified for purposes of clarity of description. In the third exemplary embodiment, during the measurement of the number of microorganisms, vessel retaining unit 20 and vessel 22 are rotated by motor 35 to increase the opportunity of bringing the microorganisms diffused widely in vessel 22 close to measurement electrode 41.

In the state in which the number of microorganisms is measured using measurement chip 39, rod-shaped manipulation body 44 constituting the measurement chip separating body is inserted in through-hole 43 in FIG. 27 provided on the intermediate portion of measurement chip 39 as illustrated in FIG. 30.

This point will be described in detail. As is clear from FIG. 29, manipulation body 44 is retreated rearward until measurement chip 39 is lowered to vessel 22. As illustrated in FIG. 30, manipulation body 44 protrudes toward the direction of front surface cover 19 before measurement chip 39 is completely lowered to vessel 22.

As can be seen from FIGS. 27, 33B, and 33C, because through-hole 43 made in measurement chip 39 is vertically long, manipulation body 44 can protrude even before measurement chip 39 is completely lowered.

As illustrated in FIG. 33C, hook-shaped engagement portion 45 is provided on a lower surface at the front end of manipulation body 44, and the lower end side of through-hole 43 of measurement chip 39 is engaged with engagement portion 45 when measurement chip 39 is separated.

In the third exemplary embodiment, the number of microorganisms in vessel 22 can be measured in the state in FIG. 30. However, as illustrated in FIG. 28, when front surface cover 19 is opened and closed after the measurement, measurement chip 39 is largely lifted out of vessel 22 along with front surface cover 19, and measurement chip 39 is in the state in which the measurement is already performed in vessel 22. That is, as illustrated in FIG. 28, when measurement chip 39 is lifted along with front surface cover 19 after the measurement, undesirably pure water 27 containing the microorganisms adhering during the measurement is carelessly spattered or drops onto the front portion or lower portion of front surface cover 19. Therefore, in the third exemplary embodiment, manipulation body 44 constituting the measurement chip separating body is provided as described above.

Specifically, when the number of microorganisms is measured using measurement chip 39, namely, when measurement electrode 41 of measurement chip 39 is dipped in pure water 27 as illustrated in FIG. 30, manipulation body 44 is already protruded in through-hole 43 of measurement chip 39.

The mechanism in FIGS. 31 and 32 causes manipulation body 44 to protrude from the state in FIG. 29 to the state in FIG. 30, and causes manipulation body 44 to retreat from the state in FIG. 30 to the state in FIG. 29. Manipulation body 44 is slidably provided on cylindrical guide tube 46, and guide tube 46 is fixed to body case 18. In guide tube 46, manipulation body 44 is always biased in the rear direction opposite to front surface cover 19 by spring 47 in FIG. 29. FIGS. 29 and 31 illustrate this state.

When front surface cover 19 is further pushed down from the state in FIG. 29 to the state in FIG. 30, namely, when measurement electrode 41 of measurement chip 39 is dipped in pure water 27, cam plate 48 is lowered from the state in FIG. 31 to the state in FIG. 32 in conjunction with the lowering operation of front surface cover 19, thereby causing manipulation body 44 to protrude onto the side of measurement chip 39. That is, because the upper portion of cam plate 48 protrudes in the front direction which is the side of front surface cover 19 (the side of measurement chip 39) compared with the lower portion of cam plate 48, the upper portion of cam plate 48 pushes manipulation pin 49 of manipulation body 44 onto the side of front surface cover 19 (the side of measurement chip 39) as cam plate 48 is lowered. As a result, manipulation body 44 invades in through-hole 43 of measurement chip 39 as illustrated in FIGS. 33B and 33C.

When manipulation body 44 protrudes onto the side of front surface cover 19 (the side of measurement chip 39), spring 47 is compressed as illustrated in FIGS. 30 and 33A.

FIGS. 35A and 35B illustrate the state immediately after front surface cover 19 is lifted by the restoring force of spring 33 in FIG. 32 after the measurement. At this point, because protruded flat surface 50 in FIG. 33 exists in the upper end portion of the cam plate 48, manipulation body 44 does not retreat but is maintained in a given position immediately after front surface cover 19 is lifted.

However, because connection electrode 40 in the upper end portion of measurement chip 39 is retained by measurement chip-retaining unit 38, connection electrode 40 is slightly lifted as front surface cover 19 is slightly lifted as illustrated in FIGS. 35A and 35B. As a result, hook-shaped engagement portion 45 of manipulation body 44 is engaged with the lower end portion of through-hole 43 of measurement chip 39 as illustrated in FIG. 35B.

FIGS. 36A and 36B illustrate the moment in which front surface cover 19 is further lifted from this state. As illustrated in FIG. 36A, manipulation pin 49 of manipulation body 44 is separated from flat surface 50 of cam plate 48 by lifting front surface cover 19, and moves to the inclination portion of cam plate 48.

As a result, manipulation body 44 retreats rearward by the restoring force of spring 47, whereby a portion below through-hole 43 of flexible measurement chip 39 is moved rearward. Then, as illustrated in FIG. 36B, the portion is pressed against the inner wall surface of vessel 22.

As described above, because hook-shaped engagement portion 45 is provided at the front end of manipulation body 44, the portion below the through-hole 43 of measurement chip 39 can stably be pulled rearward as illustrated in FIG. 36B.

On the other hand, a portion above through-hole 43 of measurement chip 39 is retained by measurement chip-retaining unit 38, the portion above through-hole 43 of measurement chip 39 is inclined forward compared with the portion below through-hole 43 of measurement chip 39.

FIG. 37 illustrates the state in which front surface cover 19 is further lifted. When front surface cover 19 is lifted to the position in FIG. 37, connection electrode 40 of measurement chip 39 is separated from measurement chip-retaining unit 38. At this point, front surface cover 19 is opened upward by handle 34 as illustrated in FIG. 28, and then measurement chip 39 is picked out from vessel 22.

In the third exemplary embodiment, one of the features is that, even if front surface cover 19 is opened, measurement chip 39 is not lifted out of vessel 22 in conjunction with the opening operation.

Therefore, even if the opening operation of front surface cover 19 is performed, pure water 27 containing the microorganisms adhering during the measurement is not carelessly spattered or does not drop onto the front portion or lower portion of front surface cover 19, so that a desirable situation is obtained from a hygiene viewpoint.

In the third exemplary embodiment, as illustrated in FIG. 37, in order to pick out measurement chip 39 retained by manipulation body 44, when connection electrode 40 in the upper end portion of measurement chip 39 is picked to slightly press connection electrode 40 in the inward direction of vessel 22 located below, measurement chip 39 is disengaged with through-hole 43 of engagement portion 45 of manipulation body 44, so that measurement chip 39 can easily drop in vessel 22. In order that measurement chip 39 drops in vessel 22, a manipulation body including front end portion 62 at the front end may be used as manipulation body 44 as illustrated in FIG. 40.

As illustrated in FIG. 38, because dropped measurement chip 39 is retained in vessel 22, the trouble is not generated from the hygiene viewpoint.

In the third exemplary embodiment, when front surface cover 19 is opened after the measurement, because measurement chip 39 and microorganism collecting tool 30 are stored in vessel 22, vessel 22 is taken out from vessel retaining unit 20, and measurement chip 39 and microorganism collecting tool 30 are discarded as the medical waste along with vessel 22.

Therefore, vessel 22, measurement chip 39, and microorganism collecting tool 30 can be discarded as the medical waste without touching pure water 27 in vessel 22.

FIG. 34 illustrates the control block diagram for performing the above operations. As illustrated in FIG. 34, motor 35 is connected to motor power supply 52 of power supply 51, and motor power supply 52 is connected to motor power supply controller 54 of controller 53. Electrode power supply 55 of power supply 51 is connected to measurement electrode 41, and electrode power supply 55 is also connected to electrode power supply controller 56. That is, electrode power supply 55 applies the 3-MHz voltage and the 800-kHz voltage to measurement electrode 41, and measurement unit 57 and calculator 58, which are connected to measurement electrode 41, simultaneously measure the number of microorganisms.

A measurement value is displayed on display unit 59 provided at the back of front surface cover 19.

Manipulation unit 60 illustrated below display unit 59 in FIG. 34 is the power supply manipulation unit. Although switch 36, display lamp 37, and measurement start switch 42 in FIG. 18 are not illustrated in FIG. 34, switch 36, display lamp 37, and measurement start switch 42 are connected to controller 53.

Fourth Exemplary Embodiment

Figure 41:
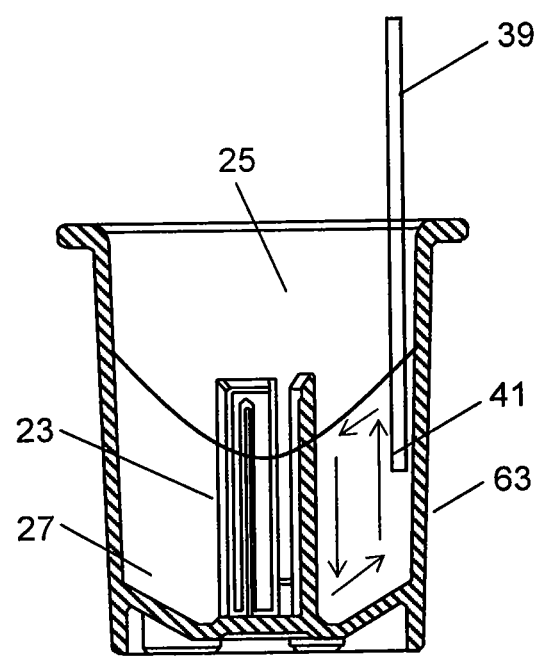
FIG. 41 is a sectional view illustrating a microorganism counting cell according to an exemplary embodiment of the present invention in measurement.

A fourth exemplary embodiment is different from the third exemplary embodiment in that, as illustrated in FIG. 41, vessel 63 having a inclined bottom surface is used instead of vessel 22 having the flat bottom surface of the third exemplary embodiment in FIG. 22.

That is, the bottom surface of vessel 63 used in the fourth exemplary embodiment is configured to be inclined upward from the outer circumferential surface of retaining body 23 vertically disposed on the bottom surface of vessel 63 to the inner wall surface of vessel 63. More specifically, the bottom surface of vessel 63 is inclined at an angle of 30 degrees.

Therefore, a water flow is formed in a vertical direction as illustrated in FIG. 41, and the microorganisms (bacteria) eluted in pure water 27 of vessel 63 increase the opportunity of coming close to measurement electrode 41 of measurement chip 39, so that the measurement time can be shortened.

More particularly, during the measurement, vessel retaining unit 20 and vessel 63 are rotated by motor 35. At this point, as illustrated in FIG. 41, the rotating shaft portion of pure water 27 is largely recessed while the outer circumferential portion (the inner surface portion of vessel 63) of pure water 27 rises. That is, a spiral swirling flow is formed in vessel 63.

At this point, the bottom surface of vessel 63 is inclined upward from the outer circumferential surface of retaining body 23 vertically disposed on the bottom surface of vessel 63 to the inner wall surface of vessel 63. Therefore, pure water 27 of vessel 63 rises along the inclination surface of the bottom surface of vessel 63 and forms a rising water flow rising along the inner wall surface of vessel 63, and pure water 27 forms a falling water flow flowing along the outer circumferential surface in the outer circumferential surface of retaining body 23. That is, the water flow is formed in the vertical direction.

The microorganisms (bacteria) eluted in pure water 27 move into the strong rising water flow to rise along the inclination surface of the vessel bottom surface, and reach measurement electrode 41 (FIG. 33A) of measurement chip 39.

Accordingly, the microorganisms (bacteria) eluted in pure water 27 of vessel 63 increase the opportunity of coming close to measurement electrode 41 of measurement chip 39. As a result, the microorganism elution time can be shortened while the measurement time is shortened.

As described above, the microorganism counting cell of the present invention includes: the bottomed cylindrical vessel that includes the upper surface opening; and the cylindrical retaining body disposed vertically on the bottom surface in the vessel, and has the collecting element provided on the lower end portion of the rod-shaped microorganism collecting tool being inserted in the retaining body from the upper surface opening, the plurality of first elution protrusions of a longwall shape formed in an axial direction of the retaining body at predetermined intervals around the interior side surface of the retaining body, and the elution grooves, each formed to cut through a side surface of the retaining body from the inside to the outside between adjoining two of the plurality of first elution protrusions.

That is, in the present invention, because the cylindrical retaining body is vertically disposed on the bottom surface in the vessel, the collecting element provided on the lower end portion of the rod-shaped microorganism collecting tool is inserted from the upper surface opening of the vessel.

At this point, because the plurality of first elution protrusions formed into longwall shape in the axial direction of the retaining body are provided at predetermined intervals in the interior side surface of the retaining body, the portion from the lower portion to upper portion of the collecting element abuts on the first elution protrusions formed into the longwall shape in the axial direction at predetermined intervals. When the microorganism collecting tool is rotated, the microorganisms can be eluted from the whole portion from the lower portion to the upper portion of the collecting element of the microorganism collecting tool.

The elution grooves, each formed to cut through a side surface of the retaining body from the inside to the outside between adjoining two of the plurality of first elution protrusions. Therefore, the microorganisms eluted from the collecting element of the microorganism collecting tool can be eluted to the vessel through the elution grooves.

As a result, the microorganism elution time can be shortened.

The eluted microorganisms can be eluted out of the retaining unit through the elution grooves, namely, into the liquid in the vessel. Therefore, the subsequent measurement can easily be performed.

INDUSTRIAL APPLICABILITY

As described above, the microorganism counting cell of the present invention includes: the bottomed cylindrical vessel that includes the upper surface opening; and the cylindrical retaining body disposed vertically on the bottom surface in the vessel, has the collecting element provided on the lower end portion of the rod-shaped microorganism collecting tool being inserted in the retaining body from the upper surface opening, the plurality of first elution protrusions of a longwall shape formed in an axial direction of the retaining body at predetermined intervals around the interior side surface of the retaining body, and the elution grooves, each formed to cut through a side surface of the retaining body from the inside to the outside between adjoining two of the plurality of first elution protrusions. Therefore, the microorganism elution time can be shortened.

That is, in the present invention, because the cylindrical retaining body is vertically disposed on the bottom surface in the vessel, the collecting element provided on the lower end portion of the rod-shaped microorganism collecting tool is inserted from the upper surface opening of the vessel.

At this point, because the plurality of first elution protrusions formed into longwall shape in the axial direction of the retaining body are provided at predetermined intervals in the interior side surface of the retaining body, the portion from the lower portion to upper portion of the collecting element abuts on the first elution protrusions formed into the longwall shape in the axial direction at predetermined intervals. When the microorganism collecting tool is rotated, the microorganisms can be eluted from the whole portion from the lower portion to the upper portion of the collecting element of the microorganism collecting tool.

The elution grooves, each formed to cut through a side surface of the retaining body from the inside to the outside between adjoining two of the plurality of first elution protrusions. Therefore, the microorganisms eluted from the collecting element of the microorganism collecting tool can be eluted to the vessel through the elution grooves.

As a result, the microorganism elution time can be shortened.

The eluted microorganisms can be eluted out of the retaining unit through the elution grooves, namely, into the liquid in the vessel. Therefore, the subsequent measurement can easily be performed.

Accordingly, the present invention is expected to be widely used as the microorganism counting cell and the microorganism counter provided with the microorganism counting cell.

REFERENCE MARKS IN THE DRAWINGS

1 Vessel
1a Fixing hole
1b Rib
1c Vessel retaining unit
1d Driving protrusion
1e Motor
2 Upper surface opening
3 Cotton swab
3a Rod
4 Collecting element
4a Swab portion
5 Retaining body
5a Side surface body
6 Elution groove
7 Elution protrusion
8 Elution protrusion
9 Pure water
10 Step portion
11 Cover body
12 Vessel support
13 Mounting unit
13a Projection
14 Rotation tool
15 Cotton swab mounting unit
16 Switch
17 Motor
18 Body case
19 Front surface cover
20 Vessel retaining unit
21 Driving protrusion
22 Vessel
23 Retaining body
24 Elution protrusion
25 Elution groove
26 Elution protrusion
27 Pure water
28 Cover
29 Protrusion
30 Microorganism collecting tool
31 Collecting element
32 Manipulation button
33 Spring
34 Handle
35 Motor
36 Switch
37 Display lamp
38 Measurement chip-retaining unit
39 Measurement chip
40 Connection electrode
41 measurement electrode
42 Measurement start switch
43 Through-hole
44 Manipulation body
45 Engagement portion
46 Guide tube
47 Spring
48 Cam plate
49 Manipulation pin
50 Flat surface
51 Power supply
52 Motor power supply
53 Controller
54 Motor power supply controller
55 Electrode power supply
56 Electrode power supply controller
57 Measurement unit
58 Calculator
59 Display unit
60 Manipulation unit
61 Rib
62 Front end portion
63 Vessel

The invention claimed is:

1. A microorganism counting cell, comprising:
a bottomed cylindrical vessel that includes an upper surface opening; and
a cylindrical retaining body disposed vertically on a bottom surface in the vessel for receiving a collecting element provided on a lower end portion of a rod-shaped microorganism collecting tool inserted therein, the retaining body disposed such that a radially exterior side surface of the retaining body is spaced from a radially interior side surface of the cylindrical vessel,
a space that is formed in a shape of substantially circular ring between an inner peripheral surface of the vessel and an outer peripheral surface of the retaining body, and in which a liquid for eluting a microorganism is filled, and
a liquid filled in the space formed between the radially exterior side surface of the retaining body and the radially interior side surface of the cylindrical vessel, and wherein
the retaining body is provided with a plurality of first elution protrusions of a longwall shape formed in an axial direction of the retaining body at predetermined intervals around a radially interior side surface of the retaining body, and elution grooves, each formed to cut through a side surface of the retaining body from the inside to the outside between adjoining two of the plurality of first elution protrusions.

2. The microorganism counting cell according to claim 1, wherein
the cylindrical retaining body is configured to retain a side surface of the collecting element of the microorganism collecting tool inserted in the retaining body such that the side surface of the collecting element is made to abut on the plurality of first elution protrusions provided on the interior side surface of the retaining body.

3. The microorganism counting cell according to claim 1, wherein
side surface bodies of an odd number are provided around the side surface of the retaining body.

4. The microorganism counting cell according to claim 1, wherein
a width of the elution groove in a circumferential direction of the retaining body is smaller than a thickness of a rod of the microorganism collecting tool inserted in the retaining body.

5. The microorganism counting cell according to claim 1, wherein
a plurality of second elution protrusions are provided circularly at equal intervals around an axis of the retaining body in an interior bottom surface of the retaining body.

6. The microorganism counting cell according to claim 1, wherein
a liquid is provided on the vessel, and a cover body is detachably provided on the upper surface opening of the vessel.

7. The microorganism counting cell according to claim 1, wherein
a coupling unit is provided on the outside of the vessel bottom surface for coupling to a rotation driving unit that rotates the vessel.

8. A microorganism counter, comprising:
a vessel retaining unit that retains the bottomed cylindrical vessel including the upper surface opening of the microorganism counting cell according to claim 1 with the opening oriented upward;
a rotation driving unit that rotates the vessel retained by the vessel retaining unit around a vertically rotating shaft;
an electrode insertion unit that inserts a measurement chip in the vessel through the opening from above the vessel retained by the vessel retaining unit; and
a measurement unit that measures a microorganism using a measurement electrode of the measurement chip that is inserted in the vessel by the electrode insertion unit.

9. The microorganism counter according to claim 8, wherein
the bottom surface of the bottomed cylindrical vessel is upwardly inclined toward an inner wall surface of the vessel.

10. The microorganism counter according to claim 8, wherein
the vessel retaining unit is configured to rotate the vessel while retaining an outer circumference of the vessel.

11. The microorganism counter according to claim 10, wherein
the vessel retaining unit is formed into a bottomed cylindrical shape including an opening in an upper surface.

12. The microorganism counter according to claim 11, wherein
the vessel retaining unit is provided with a driving protrusion that protrudes toward a coupling unit provided on the outside of the vessel bottom surface.

13. The microorganism counter according to claim 8, wherein
the electrode insertion unit includes a measurement chip-retaining unit that detachably retains the measurement chip.

14. The microorganism counter according to claim 13, wherein
the measurement chip is mounted above a horizontal position on the electrode insertion unit, and the measurement chip is inserted in the vessel by turning the measurement chip downward.

15. A microorganism counter, comprising:
a vessel retaining unit that retains the bottomed cylindrical vessel including the upper surface opening of the microorganism counting cell according to claim 1 with the opening oriented upward;
a rotation driving unit that rotates the vessel retained by the vessel retaining unit around a vertically rotating shaft;
an electrode insertion unit that inserts a measurement chip in the vessel through the opening from above the vessel retained by the vessel retaining unit; and
a measurement unit that measures a microorganism using a measurement electrode of the measurement chip that is inserted in the vessel by the electrode insertion unit, wherein
the measurement chip is detachably mounted on the electrode insertion unit, and
the microorganism counter further comprises a measurement chip separating body that retains the measurement chip while being inserted in the vessel.

16. The microorganism counter according to claim 15, wherein
the measurement chip separating body comprises a manipulation body that is inserted in a through-hole formed in the measurement chip.

17. A microorganism counter, comprising:
a body case;
a front surface cover that covers a front surface side of the body case in an openable manner;
a vessel retaining unit provided inside the body case behind the front surface cover, and retains the bottomed cylindrical vessel including the upper surface opening of the microorganism counting cell according to claim 1 with the opening oriented upward;
a rotation driving unit that rotates the vessel retained by the vessel retaining unit around a vertically rotating shaft;
an electrode insertion unit that inserts a measurement chip in the vessel through the opening from above the vessel retained by the vessel retaining unit; and
a measurement unit that measures a microorganism using a measurement electrode of the measurement chip that is inserted in the vessel by the electrode insertion unit, wherein
the measurement chip is detachably mounted on the electrode insertion unit, and
the microorganism counter further comprises a measurement chip separating body that retains the measurement chip while being inserted in the vessel.

18. The microorganism counter according to claim 17, wherein
the measurement chip separating body comprises a manipulation body that is inserted in a through-hole formed in the measurement chip, and a manipulation pin provided in the manipulation body, wherein the manipulation pin is engaged with a cam plate that is operated by opening and closing operations of the front surface cover.

19. The microorganism counter according to claim 18, wherein
the cam plate is provided with a flat surface unit that puts the manipulation pin into a non-driving state at a beginning of the opening and closing of the front surface cover.

20. A microorganism counting method using the microorganism counter according to claim 17, the method comprising:
mounting the vessel on the vessel retaining unit while the front surface cover provided on the front surface side of the body case is opened;
inserting a collecting element provided on a lower end portion of a rod-shaped microorganism collecting tool in a retaining body of the vessel;
mounting the measurement chip on the electrode insertion unit;
closing the front surface cover provided on the front surface side of the body case to have the electrode insertion unit insert the measurement chip in the vessel;

rotating the vessel by the rotation driving unit to elute a microorganism into a liquid in the vessel; and measuring a number of the microorganisms with the measurement chip of the electrode insertion unit.

* * * * *